(12) United States Patent
Venkitaraman et al.

(10) Patent No.: US 8,716,547 B2
(45) Date of Patent: May 6, 2014

(54) STRETCH LAMINATES

(75) Inventors: Anand Rudra Venkitaraman, Cincinnati, OH (US); George Stephen Reising, Batavia, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 2669 days.

(21) Appl. No.: 11/128,579

(22) Filed: May 13, 2005

(65) Prior Publication Data

US 2006/0259003 A1 Nov. 16, 2006

(51) Int. Cl.
*A61F 13/15* (2006.01)
*A61F 13/20* (2006.01)

(52) U.S. Cl.
USPC ........... 604/358; 604/361; 604/362; 604/364; 604/367; 604/368; 604/385.01; 604/385.101; 604/385.12; 604/375; 604/385.19

(58) Field of Classification Search
USPC ................ 604/358, 361, 362, 364, 367, 368, 604/385.01, 385.101, 385.12, 375, 385.19
See application file for complete search history.

(56) References Cited

U.S. PATENT DOCUMENTS

| | | | |
|---|---|---|---|
| 3,734,384 A | 5/1973 | Kozak et al. | |
| 3,734,385 A | 5/1973 | Kozak et al. | |
| 3,769,687 A | 11/1973 | Kozak et al. | |
| 3,848,594 A | 11/1974 | Buell | |
| 3,860,003 A | 1/1975 | Buell | |
| 4,381,781 A | 5/1983 | Sciaraffa et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,699,622 A | 10/1987 | Toussant et al. | |
| 4,834,735 A | 5/1989 | Alemany et al. | |
| 4,846,815 A | 7/1989 | Scripps | |
| 4,857,067 A * | 8/1989 | Wood et al. ................... 604/389 |
| 4,888,231 A | 12/1989 | Angstadt | |
| 4,894,060 A | 1/1990 | Nestegard | |
| 4,938,753 A | 7/1990 | Van Gompel et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,968,312 A | 11/1990 | Khan | |
| 4,990,147 A | 2/1991 | Freeland | |
| 5,062,840 A | 11/1991 | Holt et al. | |
| 5,092,861 A | 3/1992 | Nomura et al. | |
| 5,137,537 A | 8/1992 | Herron et al. | |

(Continued)

FOREIGN PATENT DOCUMENTS

| EP | 0820747 A1 | 1/1998 |
|---|---|---|
| WO | WO 00/37003 | 6/2000 |

*Primary Examiner* — Bhisma Mehta
*Assistant Examiner* — Ilya Treyger
(74) *Attorney, Agent, or Firm* — Kathleen Y. Carter; John G. Powell; Jay A. Krebs

(57) ABSTRACT

A stretch laminate having a first substrate is adhesively attached to an elastic film. The adhesive is applied in a continuous manner to the substrate in a first tack down region which is disposed proximate to an end of the stretch laminate. The adhesive is applied as a plurality of adhesive stripes in an activation region which is interior of the first tack down region. The adhesive stripes have a width and a distance between adjacent adhesive stripes. The ratio of stripe width to distance between the adhesive stripes is in the range of less than about 1 or greater than about 0.33.

2 Claims, 16 Drawing Sheets

(56) References Cited

U.S. PATENT DOCUMENTS

| | | | | |
|---|---|---|---|---|
| 5,147,345 | A | 9/1992 | Young et al. | |
| 5,151,092 | A | 9/1992 | Buell et al. | |
| 5,171,236 | A | 12/1992 | Dreier et al. | |
| 5,221,274 | A | 6/1993 | Buell et al. | |
| 5,242,436 | A | 9/1993 | Weil et al. | |
| 5,246,433 | A | 9/1993 | Hasse et al. | |
| 5,260,345 | A | 11/1993 | DesMarais et al. | |
| 5,269,755 | A | 12/1993 | Bodicky | |
| 5,306,266 | A | 4/1994 | Freeland | |
| 5,342,338 | A | 8/1994 | Roe | |
| 5,358,500 | A * | 10/1994 | Lavon et al. | 604/385.29 |
| 5,460,622 | A | 10/1995 | Dragoo et al. | |
| 5,499,978 | A | 3/1996 | Buell et al. | |
| 5,507,736 | A | 4/1996 | Clear et al. | |
| 5,514,121 | A | 5/1996 | Roe et al. | |
| 5,540,671 | A | 7/1996 | Dreier | |
| 5,554,142 | A | 9/1996 | Dreier et al. | |
| 5,554,145 | A | 9/1996 | Roe et al. | |
| 5,569,232 | A * | 10/1996 | Roe et al. | 604/385.3 |
| 5,569,234 | A | 10/1996 | Buell et al. | |
| 5,571,096 | A | 11/1996 | Dobrin et al. | |
| 5,580,411 | A | 12/1996 | Nease et al. | |
| 5,591,152 | A | 1/1997 | Buell et al. | |
| 5,625,222 | A | 4/1997 | Yoneda et al. | |
| 5,653,703 | A | 8/1997 | Roe et al. | |
| 5,669,897 | A | 9/1997 | Lavon et al. | |
| 5,865,823 | A | 2/1999 | Curro | |
| 5,897,545 | A | 4/1999 | Kline et al. | |
| 5,938,648 | A | 8/1999 | LaVon et al. | |
| 5,941,864 | A | 8/1999 | Roe | |
| 5,957,908 | A | 9/1999 | Kline et al. | |
| 5,977,430 | A | 11/1999 | Roe et al. | |
| 5,997,520 | A | 12/1999 | Ahr et al. | |
| 6,004,306 | A | 12/1999 | Robles et al. | |
| 6,010,490 | A | 1/2000 | Freeland et al. | |
| 6,013,063 | A | 1/2000 | Roe et al. | |
| 6,120,487 | A | 9/2000 | Ashton | |
| 6,120,489 | A | 9/2000 | Johnson et al. | |
| 6,168,584 | B1 | 1/2001 | Allen et al. | |
| 6,187,696 | B1 | 2/2001 | Lim et al. | |
| 6,189,770 | B1 | 2/2001 | Lotz | |
| 6,197,012 | B1 | 3/2001 | Mishima et al. | |
| 6,395,955 | B1 * | 5/2002 | Roe et al. | 604/361 |
| 6,399,853 | B1 * | 6/2002 | Roe et al. | 604/362 |
| 6,414,215 | B1 | 7/2002 | Roe | |
| 6,428,526 | B1 | 8/2002 | Heindel et al. | |
| 6,432,098 | B1 | 8/2002 | Kline et al. | |
| 6,664,436 | B2 * | 12/2003 | Topolkaraev et al. | 604/361 |
| 6,680,422 | B2 | 1/2004 | Roe | |
| 6,713,660 | B1 * | 3/2004 | Roe et al. | 604/361 |
| 6,837,961 | B2 | 1/2005 | Malchow et al. | |
| 2003/0233082 | A1 | 12/2003 | Kline et al. | |

\* cited by examiner

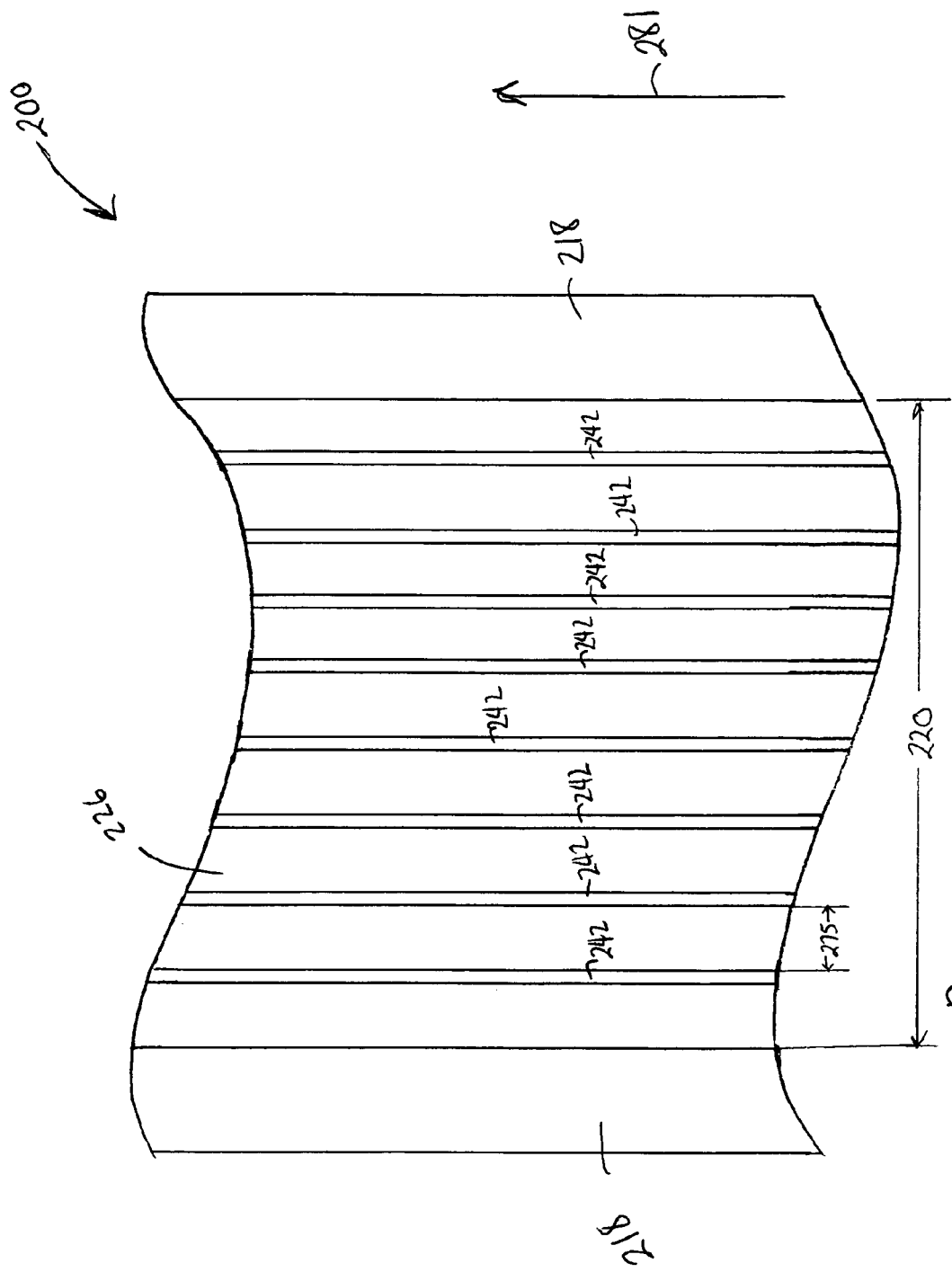

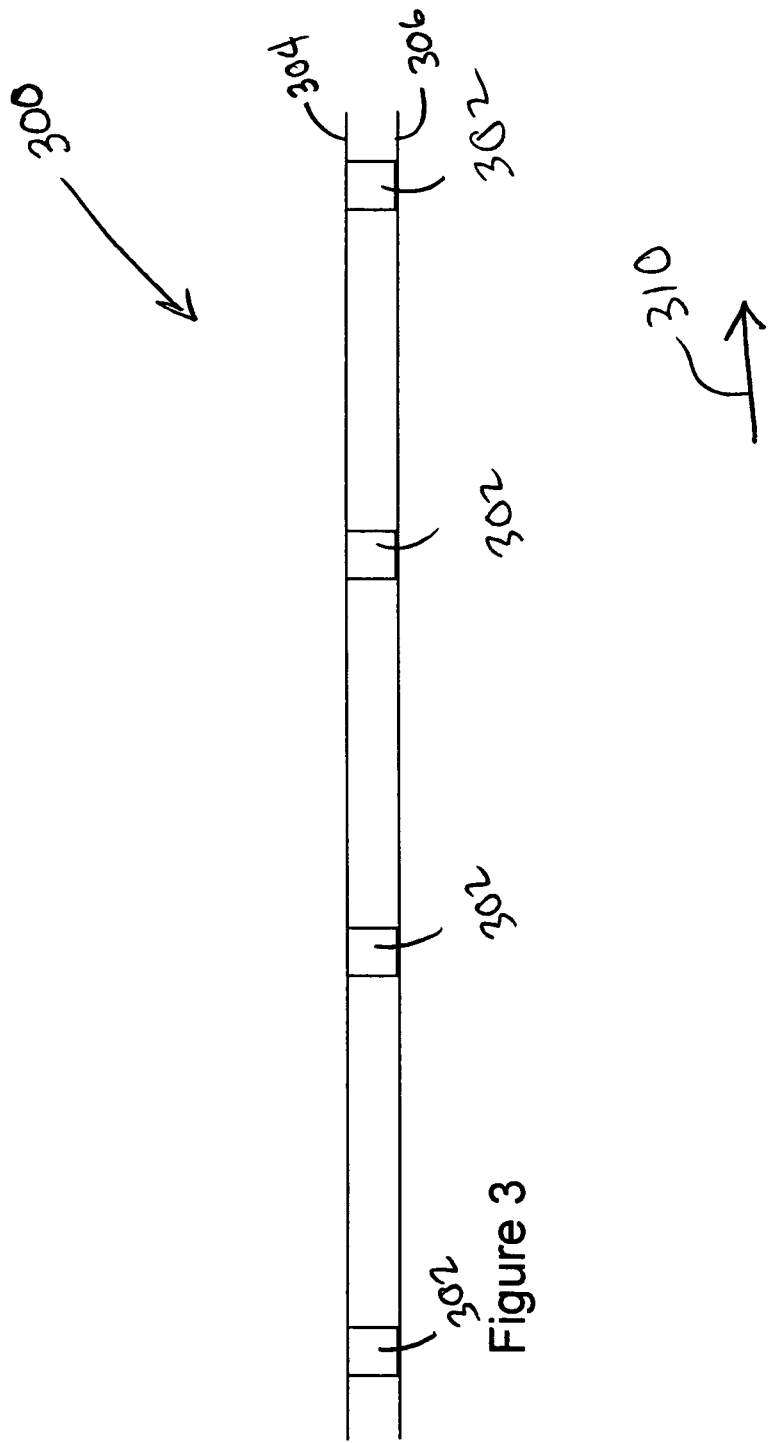

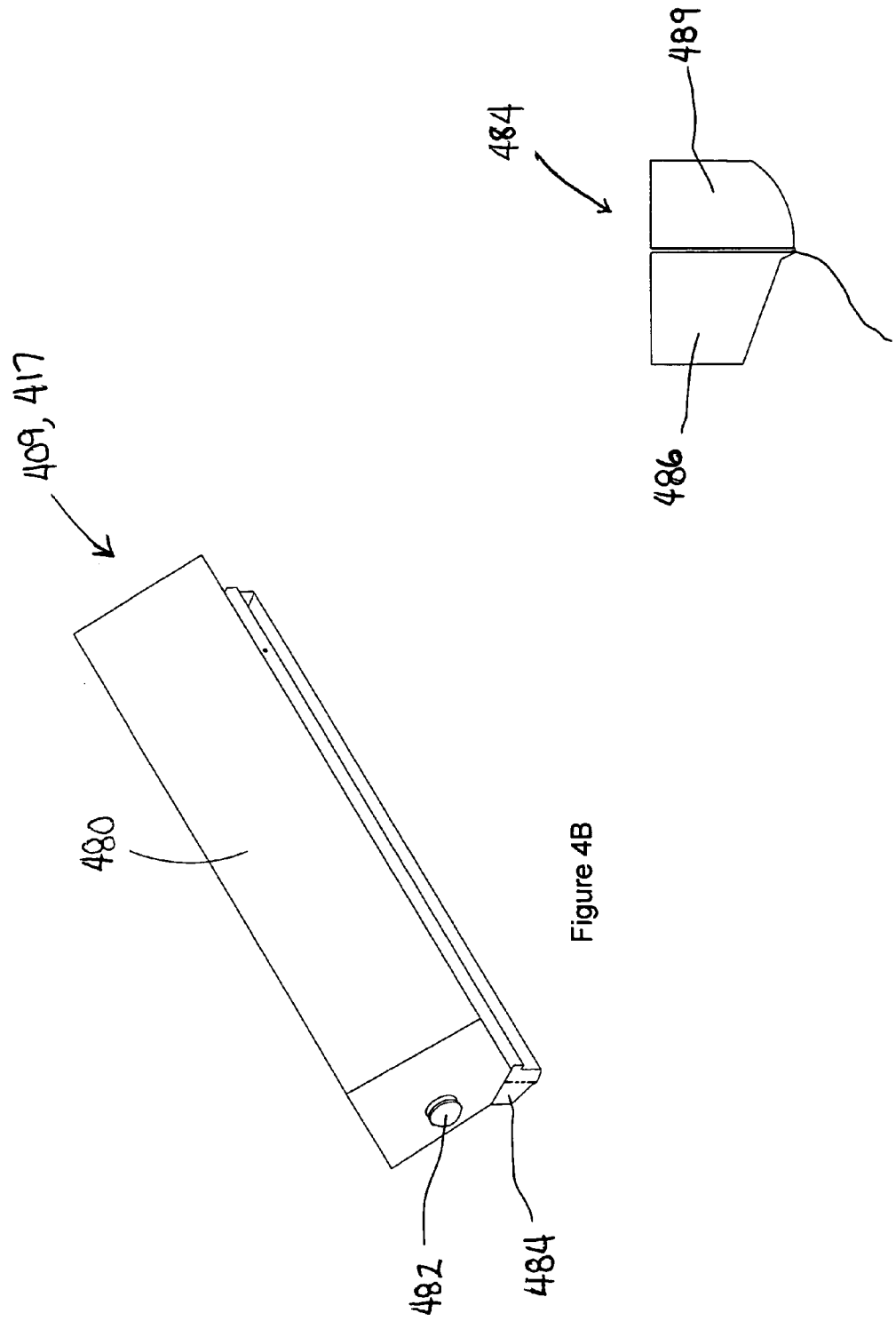

STRETCH LAMINATES

FIELD OF THE INVENTION

The present invention pertains to a stretch laminate that utilizes less adhesive than does a conventional stretch laminate. Specifically, the present invention pertains to a stretch laminate and a method of producing the same which utilizes less adhesive and can withstand the mechanical activation process while further maintaining peel force and creep resistance criteria.

BACKGROUND OF THE INVENTION

Disposable absorbent diapers are widely used by infants and incontinent individuals. In order to provide a disposable absorbent diaper which can fit a range of wearers and minimize leaks, disposable absorbent diapers often include stretch laminates. Because the wearers of disposable absorbent diapers vary in size, conventional stretch laminates are often used in the waist region and leg regions of the disposable absorbent diaper, thereby allowing the disposable absorbent diaper to fit a wide range of wearers.

A conventional stretch laminate often has at least two nonwoven materials and at least one elastic film sandwiched between the two nonwoven materials. In general, the two nonwoven materials are attached to the elastic film via an adhesive.

Conventional stretch laminates are generally elastically extensible and can be made so by meshing the conventional stretch laminate between sets of teeth. The process can involve meshing the conventional stretch laminate between activation rolls which have protruding teeth. Typically, an activation region of the conventional stretch laminate is located between the teeth while a tack down region is not significantly located between the teeth. Because the conventional stretch laminate is intermeshed between the teeth of the activation rolls, the nonwoven materials are permanently elongated at least to a certain degree, so that upon release of the applied tensile forces, the conventional stretch laminate generally will not fully return to its original undistorted configuration. Such orientation and alignment is common throughout the industry.

This process of making a stretch laminate elastically extensible is called "mechanical activation" or "ring rolling". The mechanical activation process is typically performed at high speeds. Consequently, the stretch laminate experiencing the mechanical activation process can be exposed to very high strain rates. Moreover, in order to provide the stretch laminate with greater extensibility, the stretch laminate may further be exposed to high percentages of strain.

Unfortunately, many stretch laminates incur defects as a result of the high strain rates and high percentages of strain experienced during the mechanical activation process. Many of the defects are structural in nature. For example, a nonwoven which experiences the mechanical activation process may incur defects such as holes which reduce the structural integrity of the nonwoven. Similarly, an elastic film which undergoes the mechanical activation process may also experience defects such as holes which also reduce the structural integrity of the elastic film.

It has been found that the amount of adhesive applied to a stretch laminate in an activation region, prior to mechanical activation, can influence the number of defects which the stretch laminate will incur as a result of the mechanical activation process. For example, too much adhesive in an activation region can overly restrict the movement of a multitude of fibers which make up the nonwoven. This restriction by the adhesive can lead to increased localized strains in many of these fibers. Unfortunately, the increased localized strain can lead to fracture of many of the fibers, thereby causing premature failure of the nonwoven.

In contrast, too little adhesive may reduce the localized strain in the fibers, thereby decreasing defects incurred by the stretch laminate during mechanical activation. However, because of reduced bonded area, too little adhesive can also reduce the peel force and reduce the creep resistance of the stretch laminate. Conventional wisdom teaches that less adhesive in the activation region detrimentally affects the peel force and creep resistance characteristics of the stretch laminate.

Consequently, a need for a stretch laminate which minimizes the use of adhesive while maintaining peel force values and creep resistance criteria exists. In addition, a method for making such a stretch laminates exists.

SUMMARY OF THE INVENTION

Stretch laminates constructed in accordance with the present invention utilize less adhesive while maintaining adequate peel force and creep resistance criteria. Another benefit of the present invention is that at higher strain rates, the stretch laminate may have a reduced number of defects incurred from mechanical activation.

A stretch laminate comprises a first substrate attached to an elastic film via an adhesive such that the first substrate is attached to the elastic film on a face of the elastic film. The stretch laminate further comprises at least one tack down region which is disposed proximate to an end of the stretch laminate.

An activation region is disposed interior of the tack down region. The adhesive in the activation region includes a plurality of stripes having a distance between adjacent stripes and each stripe having a stripe width. A ratio of stripe width to the distance between adjacent stripes in a portion of the activation region is less than about 1 and greater than about 0.33.

In one embodiment, a disposable absorbent article for wearing about the lower torso of a wearer may comprise a first waist region, a second waist region, and a crotch region disposed between the first waist region and the second waist region. The disposable absorbent article further comprises a chassis. In this embodiment, the chassis comprises a topsheet and a backsheet which is attached to at least a portion of the topsheet. The chassis further includes an absorbent core which is disposed between at least a portion of the topsheet and the backsheet.

The disposable absorbent article further comprises at least one elastically extensible ear panel which has an inner edge and an outer edge, wherein the inner edge is attached to the chassis in the first waist region or the second waist region. The outer edge of the ear panel can refastenably or permanently attach to the second waist region or the first waist region, respectively. The at least one elastically extensible ear panel further comprises an elastic film, a first substrate, and a second substrate. The first substrate and the second substrate are attached to the elastic film via an adhesive such that the elastic film is sandwiched between the first and second substrates. The at least one elastically extensible ear panel further comprises a first tack down region disposed along the inner edge, a second tack down region disposed along the outer edge, and an activation region disposed between the first tack down region and the second tack down region.

The adhesive in the activation region includes a plurality of stripes between the elastic layer and the first and second substrates. Each stripe of the plurality of stripes has a stripe width and a distance between adjacent stripes. A ratio of stripe width to the distance between adjacent stripes in a portion of the activation region is less than about 1 and greater than about 0.33.

A method for producing a stretch laminate is further included in the present invention. The stretch laminate has a first tack down region disposed proximate to an end of the stretch laminate and a second tack down region disposed proximate to another end of the stretch laminate, and an activation region disposed between the first tack down region and the second tack down region.

A first substrate, a second substrate, and an elastic film are provided. Adhesive is applied to a surface of the first substrate and to a surface of the second substrate in each of the first tack down region and the second tack down region. Adhesive is applied to the surfaces of the first substrate and the second substrate in the activation region as a plurality of adhesive stripes. Each adhesive stripe has a stripe width, and a distance between adjacent adhesive stripes. A ratio of stripe width to the distance between adjacent stripes in a portion of the activation region is less than about 1 and greater than about 0.33.

The first substrate, the second substrate, and the elastic film are attached such that the elastic film is sandwiched between the first substrate and the second substrate, thereby forming an intermediate laminated structure. The intermediate laminated structure is mechanically activated in the activation region such that the intermediate laminated structure experiences a strain rate of greater than or equal to about $100 \text{ s}^{-1}$, thereby forming the stretch laminate.

BRIEF DESCRIPTION OF THE DRAWINGS

The figures provided herein are not to scale.

FIG. 2B shows a plan view of the stretch laminate of FIG. 2A with a first substrate of the stretch laminate removed.

FIG. 3 shows an enlarged portion of a cross section of a stretch laminate constructed in accordance with the present invention.

FIG. 4B shows an isometric view of an adhesive applicator which can be used in the apparatus of FIG. 4A.

FIG. 4C shows an elevation view of a slot which is a component of the adhesive applicator of FIG. 4B.

DETAILED DESCRIPTION OF THE INVENTION

Definitions

Figure 1:
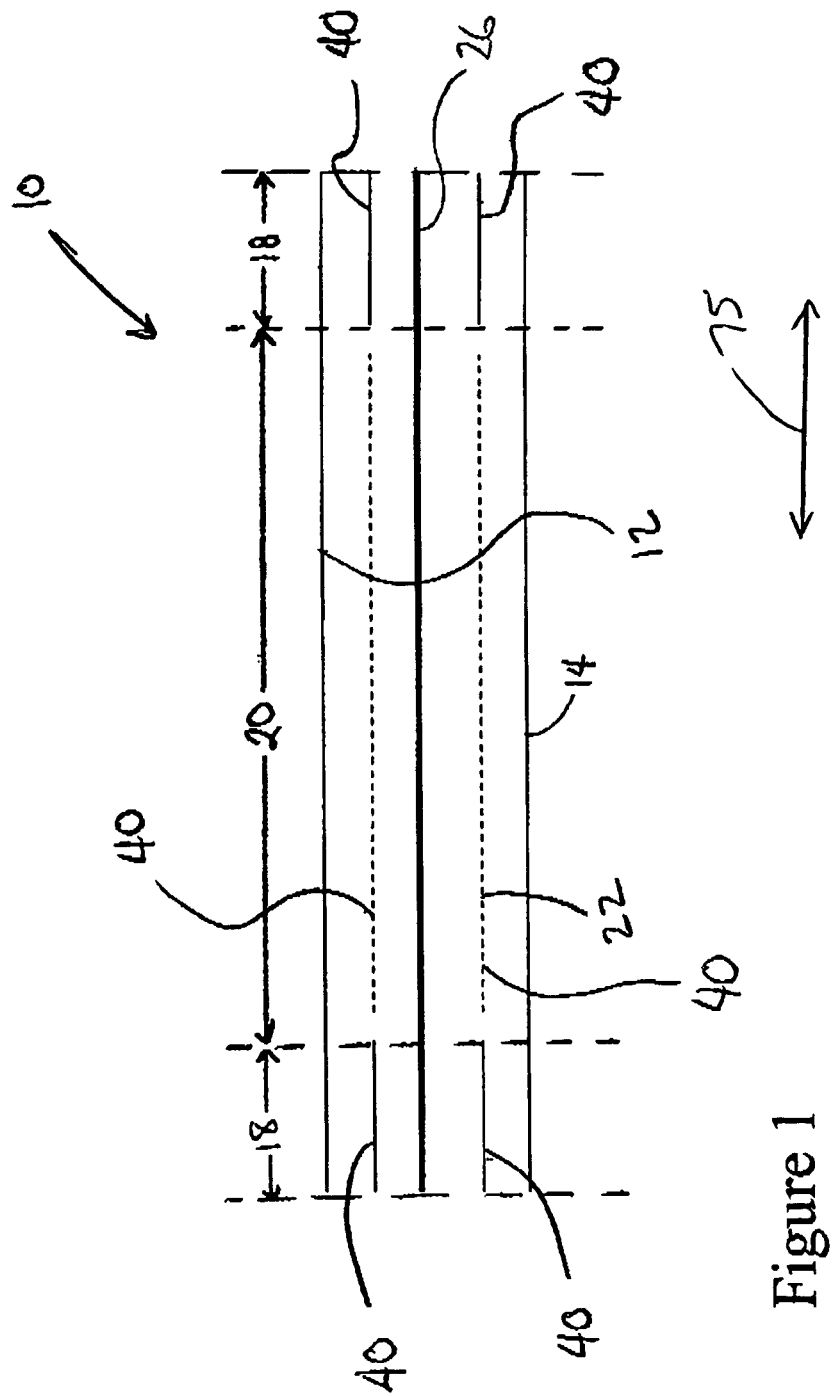
FIG. 1 shows an enlarged cross section of a conventional stretch laminate.

The following terminology is used herein consistent with the plain meaning of the terms with further details provided in the present specification.

The terms "activating", "activation", or "mechanical activation" refer to the process of making a substrate, or an elastomeric laminate more extensible than it was prior to the process.

The term "attached" refers to elements being connected or united by fastening, adhering, bonding, etc. by any method suitable for the elements being fastened, secured, or joined, together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

"Basis weight" refers to the weight of a planar material for a given surface area. Basis weight is typically measured in grams per square meter (gsm). The basis weight of a stretch laminate is typically measured while the stretch laminate is in an unstrained configuration.

The term "continuous layer" refers to a uniform coating of adhesive which can be present in the tack down regions described herein.

The term "stripes" refers to adhesive which is spaced apart, e.g. intermittent lines of adhesive.

The term "disposable" is used herein to describe products, which generally are not intended to be laundered or otherwise restored and reused for their original function. They are typically intended to be discarded after about 1 or 2 uses. It is preferred that such disposable articles be recycled, composted or otherwise disposed of in an environmentally compatible manner.

A "disposable absorbent article" refers to an article device that normally absorbs and/or retains fluids. In certain instances, the phrase refers to articles that are placed against or in proximity to the body of the wearer to absorb and contain the excreta and/or exudates discharged from the body, and includes such personal care articles as baby diapers, baby training pants, adult incontinence articles, feminine hygiene articles, baby swim diapers, wound dressings, and the like. A disposable absorbent article may be worn by infants and other incontinent persons about the lower torso.

An "elastic," "elastomer", or "elastomeric", refers to polymers or laminates exhibiting elastic properties. They include any material that upon application of a force to its relaxed, initial length can stretch or elongate to an elongated length more than 10% greater than its initial length and will substantially recover back to about its initial length upon release of the applied force.

The term "longitudinal" refers to a direction running generally parallel to the maximum linear dimension of the stretch laminate or article. Directions within ±45° of the longitudinal direction are considered to be "longitudinal".

The term "lateral" refers to a direction running from a side edge to an opposing side edge of the stretch laminate or article and generally at a right angle to the longitudinal direction and in the same plane as the longitudinal direction. Directions within ±45° of the lateral direction are considered to be "lateral".

The terms "pant", "training pant", "closed diapers", "pre-fastened diapers", "pull-on diapers", and "diaper-pants" as used herein, refer to disposable absorbent articles having a waist opening and leg openings designed for infant or adult wearers. A pant may be placed in position on the wearer by inserting the wearer's legs into the leg openings and sliding the pant into position about a wearer's lower torso. A pant can be configured such that it is preformed prior to donning the pant on the wearer, or the pant can be configured such that it is donned on the wearer and formed thereon. A pant may be preformed by any suitable technique including, but not limited to, joining together portions of the article using refastenable and/or non-refastenable bonds (e.g., seam, weld, adhesive, cohesive bond, fastener, etc.). The portions of the pant may be attached anywhere along the circumference of the article (e.g., side fastened, front waist fastened). Suitable pants are disclosed in U.S. Pat. No. 6,428,526 issued to Heindel et al.; U.S. Pat. No. 5,246,433, issued to Hasse, et al.; U.S. Pat. No. 5,569,234, issued to Buell et al.; U.S. Pat. No. 6,120,487, issued to Ashton; U.S. Pat. No. 6,120,489, issued to Johnson et al.; U.S. Pat. No. 4,940,464, issued to Van Gompel et al.; U.S. Pat. No. 5,092,861, issued to Nomura et al.; U.S. Patent Publication No. 2003/0233082 A1, entitled "Highly Flexible And Low Deformation Fastening Device", filed on Jun. 13, 2002; U.S. Pat. No. 5,897,545, issued to Kline et al.; U.S. Pat. No. 5,957,908, issued to Kline et al.

As used herein "creep resistance" refers to the ability of an elastic layer in a stretch laminate to remain attached to a substrate of the stretch laminate while the stretch laminate is under tension for an extended period of time at a predefined temperature.

As used herein "peel force" refers to the amount of force required to separate an elastic layer from a substrate of a stretch laminate. Higher peel values typically equate to less chance of delamination in use.

The term "stretch laminate" refers to a laminated structure which is elastically extensible and can be made elastically extensible by a mechanical activation process or any process known in the art.

The term "substrate" refers to a web material which is made up a plurality of fibers. The fibers can be intermeshed with one another in random or uniform patterns. Some examples of substrates are wovens, nonwovens, or a combination thereof.

The term "nonwoven" refers herein to a material made from continuous (long) filaments (fibers) and/or discontinuous (short) filaments (fibers) by processes such as spunbonding, meltblowing, carded, and the like. Nonwovens do not have a woven or knitted filament pattern. Nonwovens are typically described as having a machine direction and a cross machine direction. The machine direction is the direction in which the nonwoven is manufactured. The cross machine direction is perpendicular to and in the same plane as the machine direction. Nonwovens are typically formed with a machine direction that corresponds to the long or rolled direction of fabrication.

DESCRIPTION

Stretch laminates constructed in accordance with the present invention utilize less adhesive while maintaining adequate peel force and creep resistance criteria. Another benefit of the present invention is that at higher strain rates, the stretch laminate may have a reduced number of defects incurred from mechanical activation. The stretch laminate of the present invention can maintain peel force and creep resistance characteristics while utilizing less adhesive even at various strain rates, e.g. 100 s$^{-1}$, 200 s$^-$, 300 s$^{-1}$, or in excess of 500 s$^{-1}$.

The stretch laminate of the present invention may be incorporated into any part or element of an absorbent article. For example, the stretch laminate of the present invention may be incorporated in an ear panel which is attached to the absorbent article. In yet another example, the stretch laminate of the present invention may also be included in a waist region or leg region of a pant. The stretch laminate of the present invention can be incorporated into an absorbent article such as a diaper or a pant in any location or region where it would be desirable to incorporate the properties of a stretch laminate.

As shown in FIG. 1, a conventional stretch laminate 10 has a first nonwoven material 12 and a second nonwoven material 14. An elastic film 26 is sandwiched between the first nonwoven material 12 and the second nonwoven material 14. An adhesive 40 is disposed between the first nonwoven material 12 and the elastic film 26 and also between the second nonwoven material 14 and the elastic film 26.

The conventional stretch laminate 10 has three regions of adhesive application. Tack down regions 18 are disposed at either end of the conventional stretch laminate 10 and extend inward in a lateral direction 75. An activation region 20 is disposed between the tack down regions 18.

The adhesive 40 in the tack down regions 18 extends as a continuous layer inward from the ends of the conventional stretch laminate 10. However, the adhesive 40 in the activation region 20 is applied as a plurality of lines 22 of adhesive 40. Each of the plurality of lines 22 of adhesive 40 have a width which is 1 mm and adjacent lines 22 are spaced apart by 1 mm.

Figure 2A:
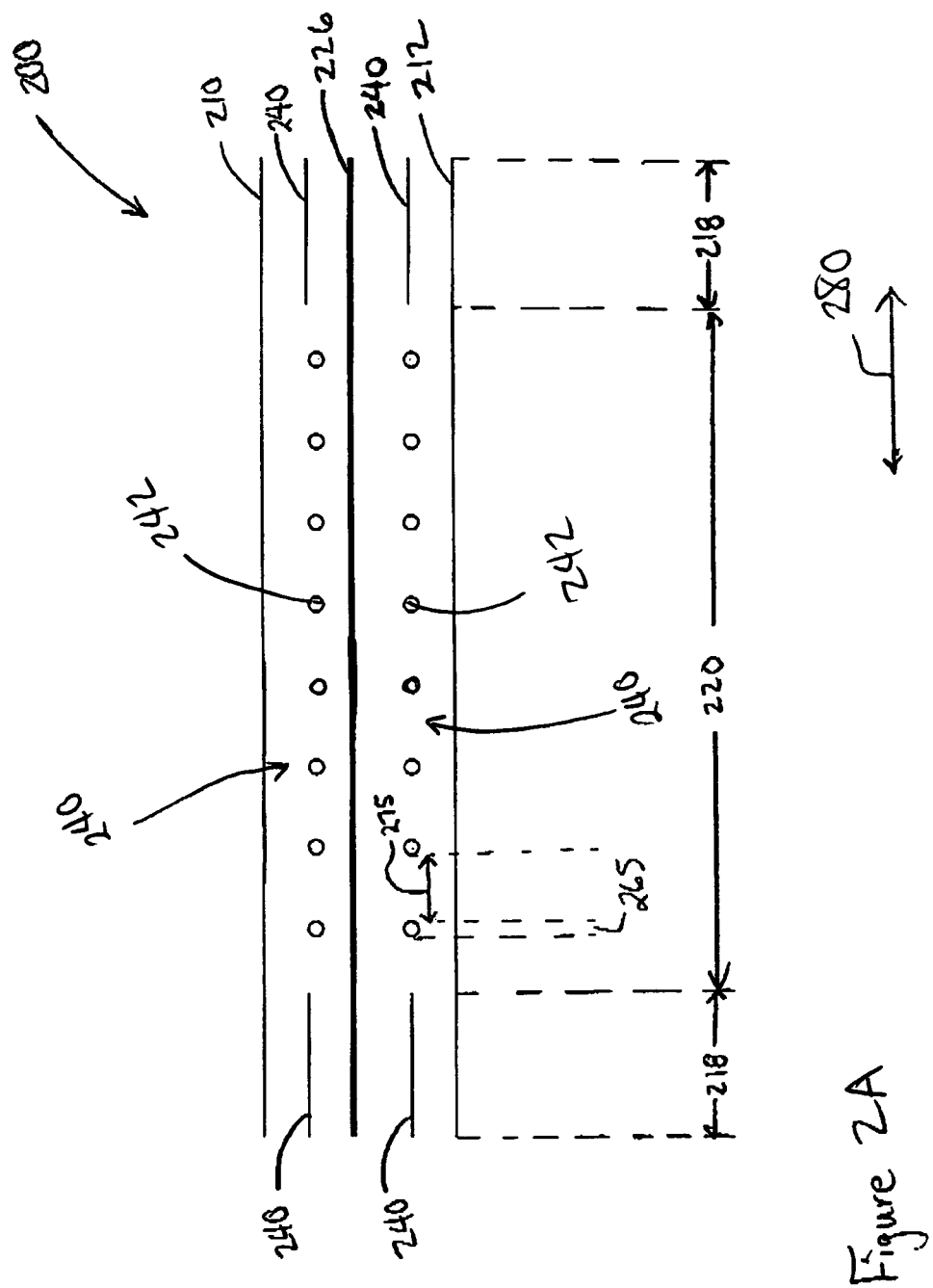
FIG. 2A shows an enlarged cross section of a stretch laminate constructed in accordance with the present invention.

As shown in FIG. 2A, similar to a conventional stretch laminate a stretch laminate 200 constructed in accordance with the present invention may comprise a first substrate 210, a second substrate 212, and an elastic film 226 sandwiched between the first substrate 210 and the second substrate 212. An adhesive 240 can be applied between the elastic film 226 and the first substrate 210 as well as between the elastic film 226 and the second substrate 212.

Also similar to a conventional stretch laminate, the stretch laminate 200 may comprise different regions. The stretch laminate 200 may comprise tack down regions 218 disposed proximate to the ends of the stretch laminate 200. Also the stretch laminate 200 may further comprise an activation region 220 which is disposed interior of the tack down regions 218.

The adhesive 240 can be applied to the stretch laminate 200 in the tack down regions 218 in a continuous manner or layer. The adhesive 240 applied in the tack down regions 218 can have a width in a lateral direction 280 which ranges from about 0.2 mm to about 10 mm from the ends of the stretch laminate 200 extending inward.

The adhesive 240 can be applied to the activation region 220 in a discontinuous manner, e.g. a plurality of adhesive stripes 242. The stretch laminate 200 may comprise adhesive 240 applied as a plurality of adhesive stripes 242 which have a width 265. Adjacent adhesive stripes 242 can be spaced apart by a distance 275 in the lateral direction 280. However, in contrast to a conventional stretch laminate, the width 265 of the adhesive stripes 242 can be less than or equal to about 1 mm while the distance 275 between the adhesive stripes 242 can be greater than 1 mm. For example, in one embodiment, the adhesive stripes 242 applied to the activation region 220 can have a width 265 of about 1 mm while the distance 275 between adjacent stripes is greater than or equal to about 1.5 mm. In another embodiment, the adhesive stripes applied to the activation region 220 can have a width 265 of about 1 mm while the distance 275 between adjacent stripes is greater than or equal to about 2 mm. In yet another embodiment, the adhesive stripes 242 applied to the activation region 220 can have a width 265 of about 1 mm while the distance 275 between the stripes is greater than or equal to about 2.5 mm. In still another embodiment, the adhesive stripes 242 applied to the activation region 220 can have a width 265 of about 1 mm while the distance 275 between the stripes is less than about 3 mm.

Also, the application of adhesive stripes 242 in the present invention is not limited to a particular width of adhesive stripe. In one embodiment, a stretch laminate constructed in accordance with the present invention can have a ratio of adhesive stripe width 265 to the distance 275 between adjacent adhesive stripes 242 which is less than about 1. In another embodiment, the ratio can be about 0.75. In yet another embodiment, the ratio can be about 0.5. In yet another embodiment, the ratio can be greater than about 0.33.

As shown in FIG. 2B, the adhesive stripes 242 can be generally parallel to a machine direction 281. The adhesive stripes 242 can be slot coated or sprayed onto their respective substrates. The adhesive stripes 242 can be continuously applied or each stripe may comprise a plurality of discrete elements. Whether the adhesive stripes 242 are continuously applied or whether they comprise a plurality of discrete elements, the adhesive stripes 242 can be arranged in a general linear or curvilinear formation. For example at least one of the plurality of adhesive stripes 242 may comprise a plurality of beads of adhesive which are generally arranged in the machine direction 281. Moreover, one or more of the plurality of adhesive stripes 242 may be continuous while the remaining number of the plurality of adhesive stripes 242 is discontinuous. Also, the adhesive in the tack down regions 218 can be applied in a similar fashion as the adhesive stripes 242.

Although not shown, the distance 275 between adjacent adhesive stripes 242 in the activation region 220 can vary within the activation region. For example, the distance between the adhesive stripes 242 in a portion of the activation region 220 may be 1.5 mm while the distance between the adhesive stripes 242 in another portion of the activation region can be 2 mm.

Also, the adhesive stripes 242 within the activation region 220 can have varying basis weights. For example, adhesive stripes 242 in a portion of the activation region 220 may have a basis weight of 6 gsm while adhesive stripes 242 in another portion of the activation region 220 can have a basis weight of 8 gsm. Similarly, the basis weight of the adhesive in the tack down regions 218 can vary from the basis weight of the adhesive in the activation region 220.

Due to the variances in the distance between adjacent adhesive stripes and in basis weight of adhesive stripes, the stripe widths and ratios discussed above can be applicable to portions of the activation region. Alternatively, the stripe widths and ratios discussed above can, in some embodiments, apply to the activation region as a whole.

Contrary to conventional wisdom, it has been determined that even when the distance 275 between the adhesive stripes 242 is about 2 mm, the stretch laminates of the present invention are able to achieve peel force values which are similar to or greater than that of a conventional stretch laminate. Data are provided hereafter where stretch laminates constructed in accordance with the present invention generally exhibit peel force values which are greater than or within 20% of the peel force values exhibited by a conventional stretch laminate. Consequently, a stretch laminate constructed in accordance with the present invention can use 20%, 30%, or up to 50%, less adhesive than does a conventional stretch laminate while maintaining adequate peel force criteria.

In addition to the peel force values, a stretch laminate constructed in accordance with the present invention may exhibit a creep resistance which is similar to that of the conventional stretch laminate. Note that because the creep resistance evaluation is objective, e.g. the stretch laminate either passes or fails the creep resistance test, there is no subjective comparison between a conventional stretch laminate and a stretch laminate constructed in accordance with the present invention. However, data are provided hereafter where stretch laminates constructed in accordance with the present invention pass the creep resistance test. Test methods for measuring the peel force as well as the creep resistance for a stretch laminate are provided hereafter.

There are many factors which may contribute to this phenomenon which is contrary to conventional wisdom. However, without wishing to be bound by theory, it is believed that adhesive interaction between an elastic film and a substrate can greatly reduce the ability of the substrate to stretch during the mechanical activation process. It is further believed that stretch laminates have restricted zones which are created by adhesive interaction and non-restricted zones which are created due to an absence of adhesive. For example, the conventional stretch laminate 10 (see FIG. 1), includes adhesive stripes in its activation region which are applied 1 mm wide and spaced apart by 1 mm. Thus, it is believed that for every 1 mm of adhesive applied, an effective restricted zone is created which is 1 mm wide. Also, it is believed that for every space of 1 mm between the 1 mm adhesive stripes, that an effective non-restricted zone is created which is 1 mm wide. Thus, the application of adhesive stripes which are 1 mm wide and spaced apart by 1 mm can effectively create restricted zones which amount to 50% of the stretch laminate and non-restricted zones which are 50%.

It is further believed that the non-restricted zones bear a larger portion of a strain load than does a restricted zone. For example, a strain of 200% applied to a conventional stretch laminate constructed as described above and having an initial width of 10 mm can have a fully extended length of 20 mm after the applied strain is released. If an assumption is made that the restricted zones carry none of the applied load, the non-restricted zones have to effectively stretch 200%.

As shown in FIG. 3, in contrast to a conventional stretch laminate, a stretch laminate 300 constructed in accordance with the present invention increases the amount of non-restricted zones of the stretch laminate 300. The stretch laminate 300 can comprise adhesive stripes 302 which attach a substrate 304 to an elastic film 306. If the adhesive stripes 302 are 1 mm wide and are spaced apart by 1.5 mm, the amount of non-restricted zones can increase to about 60% of the stretch laminate 300 over the 50% in the conventional stretch laminate.

Similar to the conventional stretch laminate, a 200% strain applied to the stretch laminate 300 having an initial width of 10 mm can cause the stretch laminate 300 to have a fully extended length of 20 mm. However, in contrast to the conventional stretch laminate, the non-restricted zones of the stretch laminate 300 may have to effectively stretch only 166%.

Note that the examples of the strain experienced by the non-restricted zones provided above are provided for illustrative purposes only. The relationship between the strain experienced by a non-restricted zone and a restricted zone may not be linear in nature.

Figure 4A:
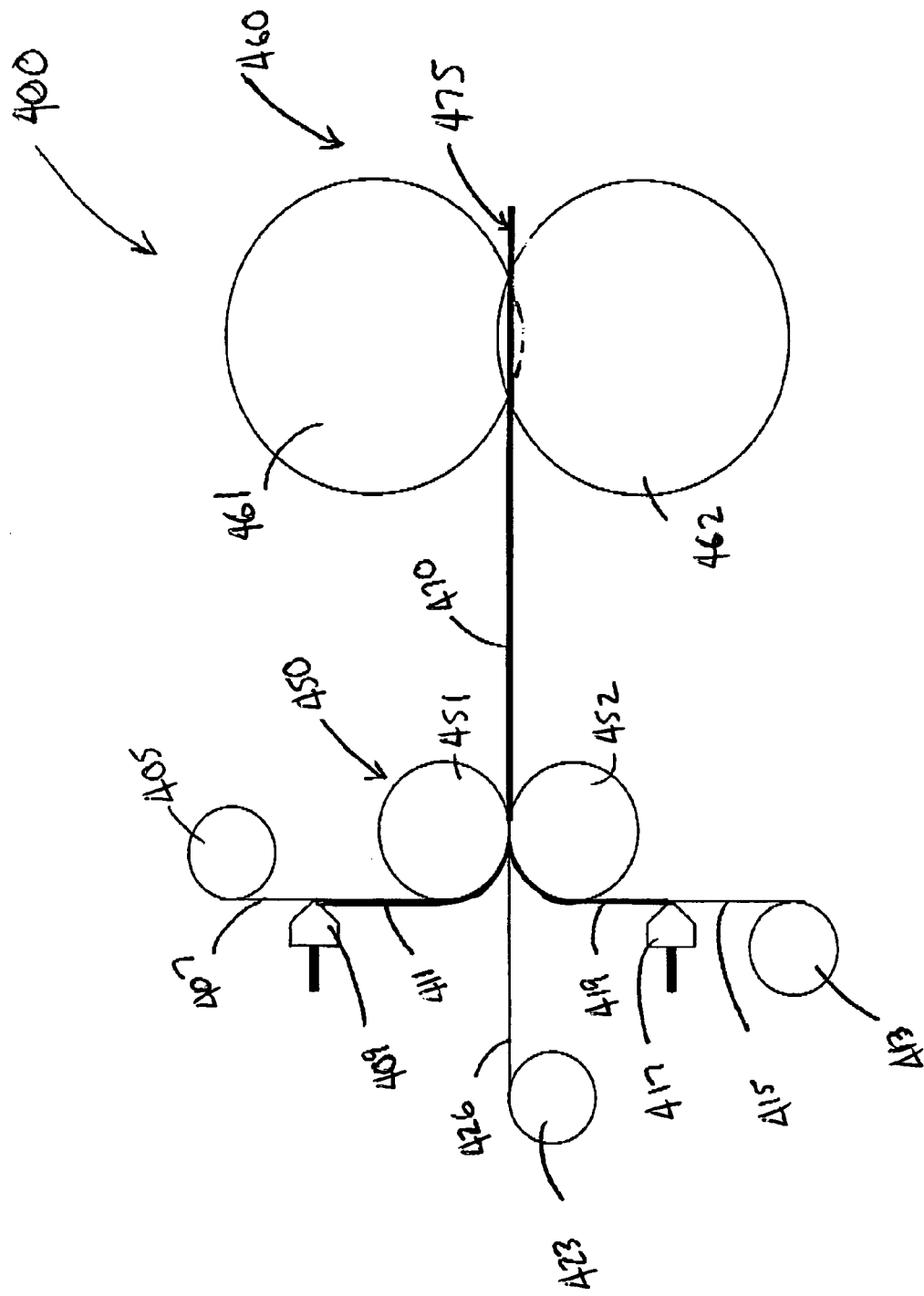
FIG. 4A shows a schematic of an apparatus which can create an elastically extensible stretch laminate in accordance with the present invention.

As shown in FIG. 4A, a stretch laminate 475 can be constructed in accordance with the present invention, for example, via an apparatus 400. The apparatus 400 comprises a first substrate supply 405 which feeds a first substrate 407 to a nipping member 450. Prior to entering the nipping member 450, an adhesive 411 can be applied to a surface of the first substrate 407 via a first adhesive applicator 409.

An elastic film 426 is also provided to the nipping member 450 via an elastic film supply roll 423. Optionally, the stretch laminate 475 may further comprise a second substrate 415 which is supplied to the nipping member 450 via a second substrate supply 413. If the stretch laminate 475 includes the second substrate 415, a second adhesive applicator 417 can apply adhesive 419 to a surface of the second substrate.

The first substrate 407, second substrate 415, and elastic film 426, may all be provided to the nipping member 450 which has a first roll 451 and a second roll 452. The nipping member 450 forms a nip in between the first roll 451 and the second roll 452 which can apply pressure to the first substrate 407, the second substrate 415, and the elastic film 426, as they pass through the nipping member 450. The first substrate 407, the second substrate 415, and the elastic film 426, can be combined to form an intermediate laminated structure 470.

The intermediate laminated structure 470 can be fed to an activation member 460 to activate the intermediate laminated structure 470 and thereby form the stretch laminate 475. The activation member 460 may include a first activation roll 461 and a second activation roll 462 each of which have a plurality of teeth. The teeth from the first activation roll 461 and the teeth of the second activation roll 462 engage the intermediate laminated structure 470. As the intermediate laminated structure 470 passes through the activation member 460, the first substrate 407 and the second substrate 415 can be permanently elongated at least to a certain degree.

Figure 4D:
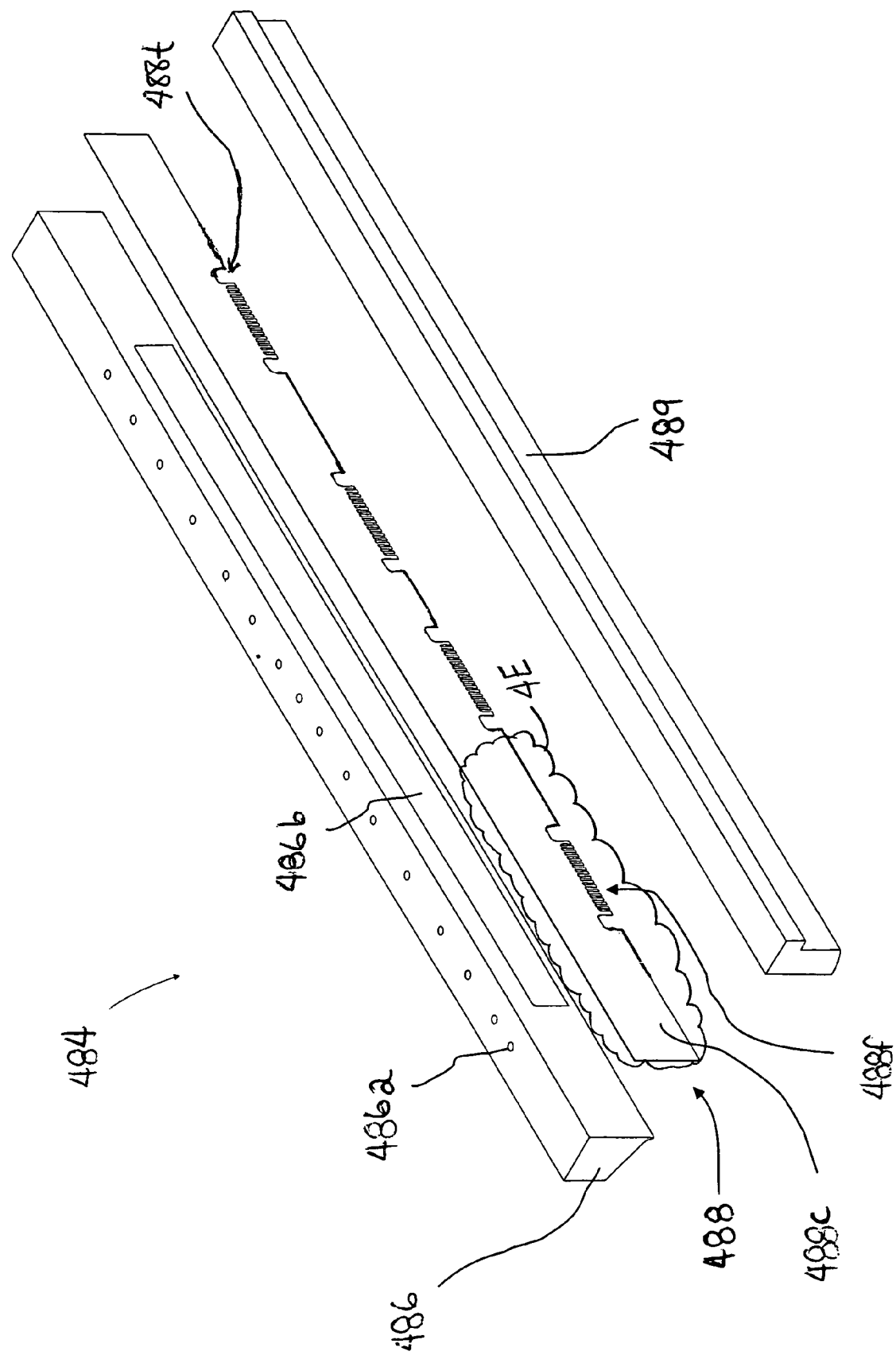
FIG. 4D shows an exploded view of the slot of FIG. 4C.

As shown in FIGS. 4B-4D the adhesive applicators 409 or 417, may comprise a multitude of elements. For the sake of explanation, reference shall only be made to the first adhesive applicator 409; however, the description provided below for the first adhesive applicator 409 is equally applicable to the second adhesive applicator 417.

As shown in FIG. 4B, the first adhesive applicator 409 may comprise a manifold 480, an adhesive inlet 482 and a slot 484. As shown in FIG. 4C, the slot 484 may comprise a backplate 486, shim 488, and a front plate 489. As shown in FIG. 4D, the backplate 486 may comprise of a plurality of adhesive inlet ports 486a. Adhesive may be introduced into slot 484 through the adhesive inlet ports 486a. The adhesive may then exit through an adhesive outlet port 486b, whereupon the adhesive can come into contact with shim 488. Shim 488 may comprise multiple regions including a closed portion 488c, an open portion 488t, and a partitioned section 488f. Suitable adhesive applicators are commercially available under the model numbers EP11, EP45, EP51, and manufactured by Nordson Corporation located in Westlake, Ohio, U.S.A.

Figure 4E:
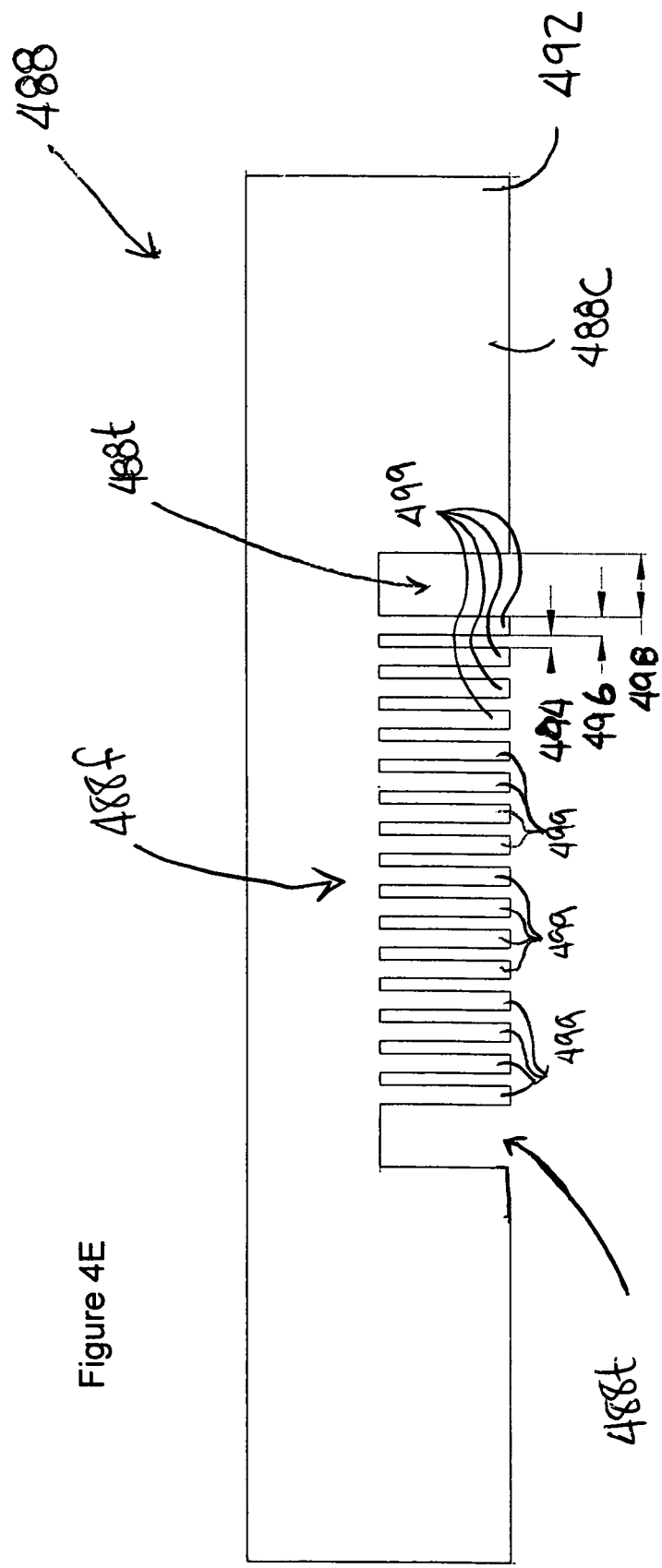
FIG. 4E shows a portion of a shim which can be utilized in the slot of FIGS. 4C and 4D.

FIG. 4E shows a portion 492 of the shim 488 which can be used to apply adhesive in the both the tack down regions and activation region (see FIG. 2) of a stretch laminate constructed in accordance with the present invention. The open portions 488t correspond to the tack down regions of the stretch laminate while the partitioned section 488f corresponds to the activation region.

As shown, the open portions 488t have a width 498 which is 5 mm. As discussed previously, the width 498 of the tack down regions, which correspond to the open portions 488t, can vary in width.

The partitioned section 488f, as shown comprises a plurality of protrusions 499 which correspond to the distance between the adhesive stripes. The protrusions 499 can have a protrusion width 496 which ranges from greater than about 1 mm to less than about 3 mm. A space 494 between the protrusions 499 corresponds to the adhesive stripe width. The space 494 as shown is about 1 mm but can vary from about 0.2 mm to about 3 mm.

As stated previously, a stretch laminate constructed in accordance with the present invention can be used in a wide variety of different absorbent articles in a wide variety of different locations. For example, a stretch laminate constructed in accordance with the present invention may be incorporated into a diaper as a side panel (see FIG. 5). In another example, a stretch laminate constructed in accordance with the present invention can be used in an ear panel or side panel of a pull-on diaper.

Figure 5:
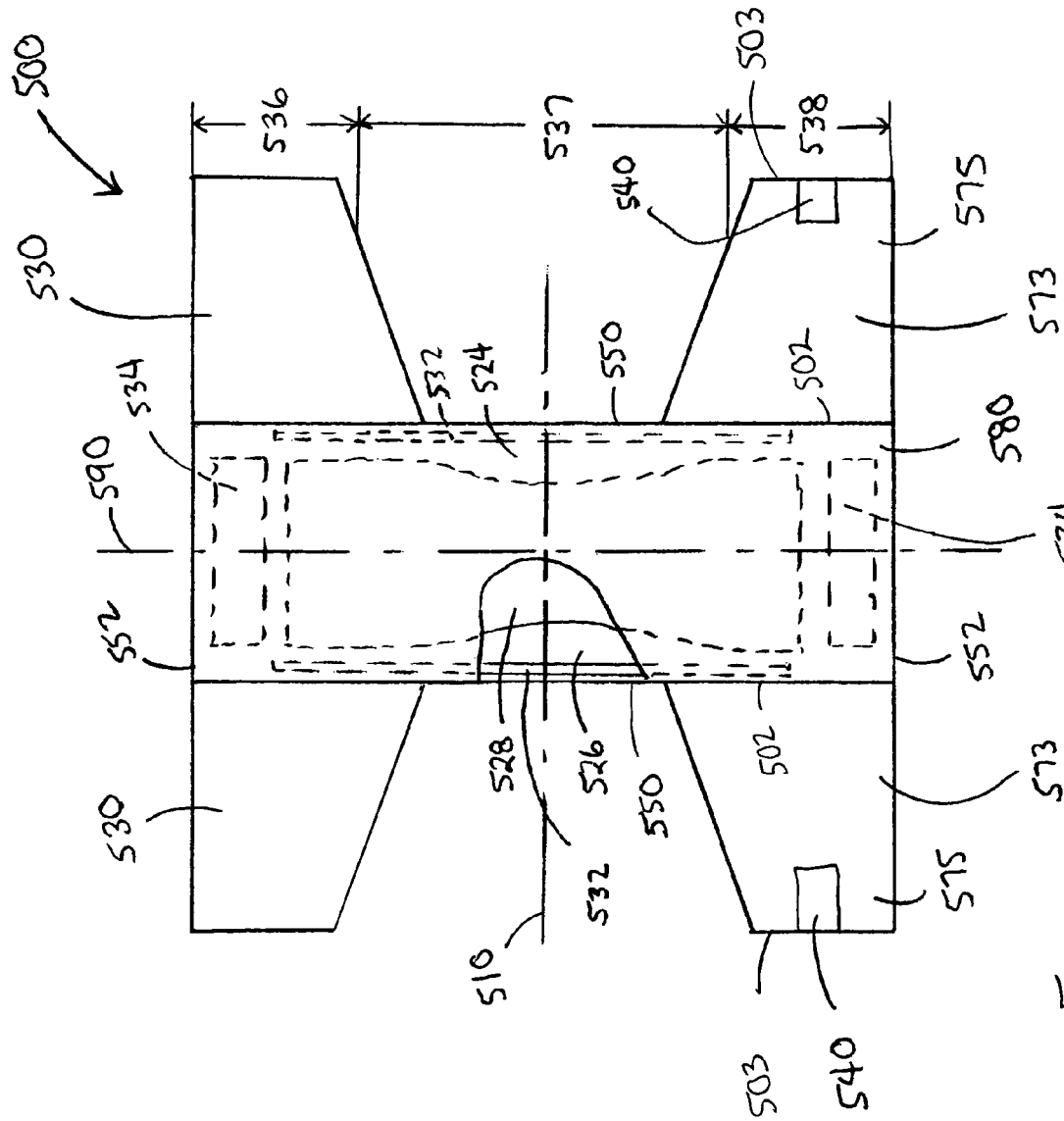
FIG. 5 shows plan view of a disposable absorbent article which may comprise a stretch laminate which is constructed in accordance with the present invention.

As shown in FIG. 5, a stretch laminate 575 of the present invention can be utilized in an ear panel 573 on a diaper 500. The portion of the diaper 500 that faces a wearer is oriented towards the viewer. As shown in FIG. 5, the diaper 500 comprises a chassis 580, a first waist region 536, a second waist region 538 opposed to the first waist region 536, and a crotch region 537 located between the first waist region 536 and the second waist region 538.

The chassis 580 comprises a topsheet 524; a backsheet 526; and an absorbent core 528 that is positioned between at least a portion of the topsheet 524 and the backsheet 526. The chassis 580 may further comprise elasticized leg cuffs 532 and elastic waist features 534. The elasticized leg cuffs 532 can extend proximate to longitudinal edges 550 from the first waist region 536 to the second waist region 538. The elastic waist features 534 can be disposed proximate to end edges 552 in the first waist region 536 and the second waist region 538.

The periphery of the chassis 580 is defined by the outer edges of the chassis 580 in which the longitudinal edges 550 run generally parallel to a longitudinal centerline 590 of the diaper 500, and the end edges 552 run between the longitudinal edges 550 generally parallel to a lateral centerline 510 of the diaper 500.

The diaper 500 may further comprise side panels 530 and ear panels 573. As shown, the side panels 530 can extend outward from the first waist region 536 and may be elastically extensible. Also, as shown, the ear panels 573 can extend outward from the second waist region 538 and may comprise the stretch laminate 575 of the present invention as well as a fastening member 540. Note that the side panels 530 may also comprise a stretch laminate constructed in accordance with the present invention.

The ear panels 573 comprise an inner edge 502 which can be attached to the second waist region 538 and an outer edge 503. The fastening member 540 can be disposed proximate to the outer edge 503. The fastening member 540 of the ear panel 573 can attach to the first waist region 536 to either the chassis 580 or the side panels 530. In another embodiment, the inner edge 502 of the ear panels 573 can be attached to the first waist region 536 such that the fastening member 540 can attach to the second waist region 538 to form an assembled diaper.

In another embodiment, the stretch laminate of the present invention may be utilized in a pull-on diaper. The stretch laminate may be used in an ear panel or side panel which is used to join a front region with a back region of the pull-on diaper. Examples of diapers with elasticized side panels which may utilize a stretch laminate of the present invention are disclosed in U.S. Pat. No. 4,857,067, U.S. Pat. No. 4,381,781, U.S. Pat. No. 4,938,753, U.S. Pat. No. 5,151,092, U.S. Pat. No. 5,221,274, U.S. Pat. No. 5,669,897, and U.S. Pat. No. 6,004,306.

The stretch laminate of the present invention can be created from a variety of materials. For example, a substrate of the present invention may comprise a nonwoven web. A suitable nonwoven for use in the present invention can comprise fibers made of polypropylene, polyethylene, polyolefins, polyester, nylon, cellulose, polyamide, bicomponent fibers, or any combination thereof. The basis weight of the nonwoven can be any suitable basis weight but will typically be in the range from about 8 gsm to about 40 gsm.

Any process known in the art may be used to make the nonwovens. Exemplary processes include spunbond, spunbond meltblown spunbond (SMS), spunbond meltblown meltblown spunbond (SMMS), carded and the like. Particularly acceptable nonwovens include high elongation carded (HEC) nonwovens and deep activation polypropylene (DAPP) nonwovens.

The fibers of the nonwovens may be bonded internally, and include fibers that are needle punched, hydro entangled, spun bonded, thermally bonded, bonded by various types of chemical bonding such as latex bonding, powder bonding, and the like. Some suitable nonwovens are mentioned in the data included herein.

The adhesive of the present invention may comprise styrene-olefin-styrene triblock copolymers such as styrene-isoprene-styrene, styrene-butadiene-styrene, or combinations thereof. The basis weight of the adhesive is typically in a range from about 4 gsm to about 28 gsm. Note that the basis weight of the adhesive is measured as the total amount of adhesive over the areas of the surfaces which the adhesive covers instead of calculated over the entire surface area of the substrate to which the adhesive is applied. Some suitable adhesives are mentioned in the examples included herein.

The elastic films of the present invention may comprise polypropylene, polyethylene, polyolefins, styrene-isoprene-styrene, styrene-butadiene-styrene, or combinations thereof. The basis weight of the films can be any suitable basis weight, but typically will be in a range from about 10 gsm to about 100 gsm. Some suitable films are mentioned in the examples included herein.

A variety of materials can be utilized in the manufacture of the absorbent articles, e.g. diapers and pull-on diapers, described herein. Some examples of the materials which can be used in the manufacture of absorbent articles are provided below; however, the list of materials provided is by no means exhaustive. For example, breathable materials, which are used extensively in absorbent articles may include materials such as woven webs, nonwoven webs, composite materials such as film-coated nonwoven webs, microporous films such as manufactured by Mitsui Toatsu Co., of Japan under the designation ESPOIR NO™ and by Exxon Chemical Co., of Bay City, Tex., U.S.A., under the designation EXXAIRE™, and monolithic films such as manufactured by Clopay Corporation, Mason, Ohio, U.S.A., under the name HYTREL™ blend P18-3097. Some breathable composite materials are described in greater detail in U.S. Pat. No. 6,187,696; U.S. Pat. No. 5,938,648; U.S. Pat. No. 5,865,823; and U.S. Pat. No. 5,571,096.

The backsheet is generally that portion of the diaper positioned adjacent a garment-facing surface of the absorbent core that prevents the exudates absorbed and contained therein from soiling articles that may contact the diaper, such as bedsheets and undergarments. The topsheet is preferably positioned adjacent body-facing surface of the absorbent core and may be joined thereto and/or to the backsheet by any attachment means known in the art. The topsheet, the backsheet, and the absorbent core may be assembled in a variety of configurations, as further described generally in U.S. Pat. No. 3,860,003, U.S. Pat. No. 5,151,092, U.S. Pat. No. 5,221,274, U.S. Pat. No. 5,554,145, U.S. Pat. No. 5,569,234, U.S. Pat. No. 5,580,411, and U.S. Pat. No. 6,004,306.

The absorbent core may comprise any absorbent material which is generally compressible, conformable, non-irritating to the wearer's skin, and capable of absorbing and retaining liquids such as urine and other certain body exudates. The absorbent core may be manufactured in a wide variety of sizes and shapes and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures for use as the absorbent core are described in U.S. Pat. No. 4,610,678, U.S. Pat. No. 4,673,402, U.S. Pat. No. 4,834,735, U.S. Pat. No. 4,888,231, U.S. Pat. No. 5,137,537, U.S. Pat. No. 5,147,345, U.S. Pat. No. 5,342,338, U.S. Pat. No. 5,260,345, U.S. Pat. No. 5,387,207, and U.S. Pat. No. 5,625,222.

As noted above, the diaper may also include a fastening system. The fastening system preferably maintains the first waist region and the second waist region in a configuration so as to provide lateral tensions about the circumference of the diaper to hold the diaper on the wearer. The fastening system may comprise a surface fastener such as tape tabs, hook and loop fastening components and/or hermaphroditic fastening components, although any other known fastening means are generally acceptable. In alternative embodiments, opposing sides of the article may be seamed or welded to form a pant. This allows the article to be used as a pull-on type diaper, such as a training pant.

Some exemplary surface fastening systems are disclosed in U.S. Pat. No. 3,848,594, U.S. Pat. No. 4,662,875, U.S. Pat. No. 4,846,815, U.S. Pat. No. 4,894,060, U.S. Pat. No. 4,946,527, U.S. Pat. No. 5,151,092, and U.S. Pat. No. 5,221,274. An exemplary interlocking fastening system is disclosed in co-pending U.S. Pat. No. 6,432,098. The fastening system may also: provide a means for holding the article in a disposal configuration as disclosed in U.S. Pat. No. 4,963,140; include primary and secondary fastening systems, as disclosed in U.S. Pat. No. 4,699,622; provide means to reduce shifting of overlapped portions or to improve fit as disclosed in U.S. Pat. No. 5,242,436; and provide means to resist gapping at a wearer's belly as disclosed in U.S. Pat. No. 5,499,978, U.S. Pat. No. 5,507,736, and in U.S. Pat. No. 5,591,152. Absorbent articles discussed herein may also include refastenable fastening elements which are known in the art.

Suitable absorbent and nonabsorbent sublayers are described in European Patent Application No. EP 0 847 738 A1 and U.S. Pat. No. 5,941,864. Further, the sublayer, or any portion thereof, may include or be coated with a lotion or other known substances to add, enhance or change the performance or other characteristics of the element.

Embodiments of the present invention may also include pockets for receiving and containing waste, spacers which provide voids for waste, barriers for limiting the movement of waste in the article, compartments or voids which accept and contain waste materials or any combinations thereof. Examples of pockets and spacers for use in absorbent products are described in U.S. Pat. No. 5,514,121, U.S. Pat. No. 5,171,236, U.S. Pat. No. 5,397,318, U.S. Pat. No. 5,540,671, U.S. Pat. No. 6,168,584, U.S. Pat. No. 5,306,266, and U.S. Pat. No. 5,997,520. Examples of compartments or voids are disclosed in U.S. Pat. No. 4,968,312, U.S. Pat. No. 4,990,147, U.S. Pat. No. 5,062,840, and U.S. Pat. No. 5,269,755. Examples of suitable transverse barriers are described in U.S. Pat. No. 5,554,142, U.S. Pat. No. 6,010,490, and U.S. Pat. No. 5,653,703. Examples of other structures especially suitable for management of low viscosity feces are disclosed in U.S. Pat. Nos. 5,941,864, 5,977,430, and 6,013,063.

Embodiments of the present invention may include barrier leg cuffs, acquisition layers, and dusting layers, each of which are well known in the art. Acquisition layer are further discussed in U.S. Pat. No. 5,460,622. Dusting layers are further discussed in U.S. Pat. No. 4,888,231.

Test Methods:

The test method for determining the peel strength of a stretch laminate is discussed below. All of the steps associated with this test method, e.g. preparing the sample and determining the peel force of a stretch laminate, should be performed in an environment of 23±1° C. and 50%±2% relative humidity.

Required Equipment:
1. A tensile testing machine available from Instron Engineering Corp. of Canton, Mass. available under the model #'s 4200, 4300, 4500, or 5500 series is used. Note that the tensile tester should be interfaced with a computer loaded with the Instron® Merlin™ Material Testing Software which controls the testing parameters, performs data acquisition and calculation, and provides graphs and data reports.
2. Select a load cell such that the forces measured will not exceed 80% of the capacity of the load cell or the load range used (e.g., typically, a 10N, 50N or 100N load cell).
3. Light duty jaws for use on the tensile tester. The light duty jaws used for the test are wider than the sample. Typically, 2.54 cm (1") wide grips are used. The grips are air-actuated and designed to concentrate the entire gripping force along a plane perpendicular to the direction of testing stress.

Equipment Preparation:
1. Calibrate tensile tester in accordance with the manufacturer's instructions.
2. Set the gauge length of the tensile tester to 5.1 cm.
3. Set the cross head speed of the tensile tester to 30.5 cm/min.
4. Set the crosshead travel to 25 cm.
5. Program computer interfaced with tensile tester to calculate average peel force in grams, disregarding data from the start of peel for the first 3 cm of the test.
6. Set the gauge length at 2.54 cm (1").

Figure 6A:
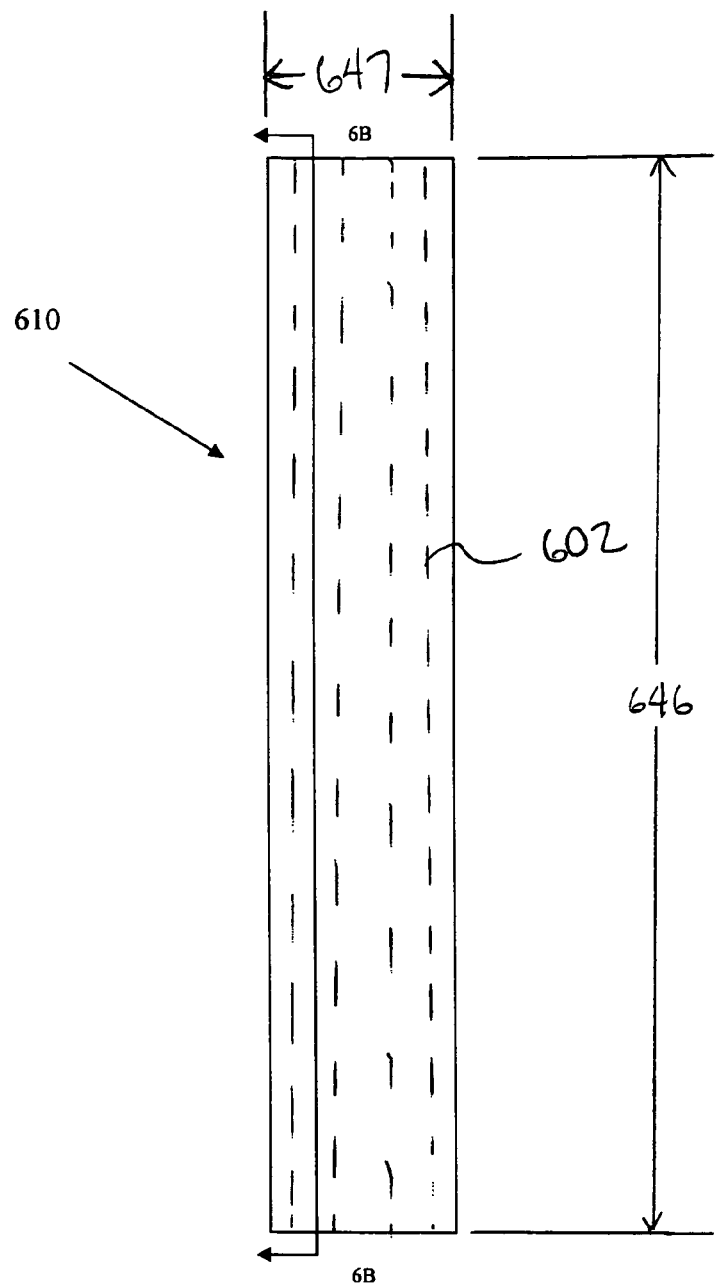
FIG. 6A shows a plan view of a sample of a stretch laminate constructed in accordance with the present invention.
Figure 6B:
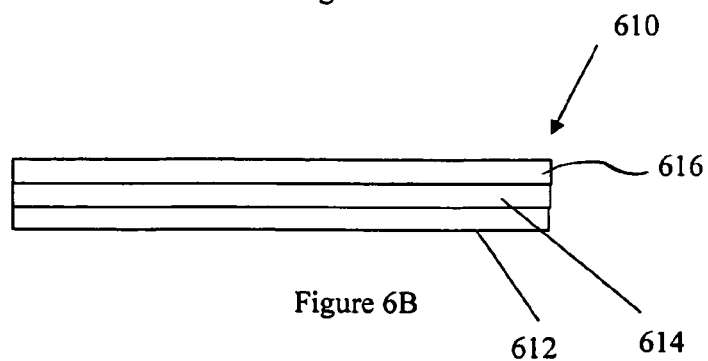
FIG. 6B shows a cross section of the sample of FIG. 6A cut along the line 6B-6B.
Figure 6C:
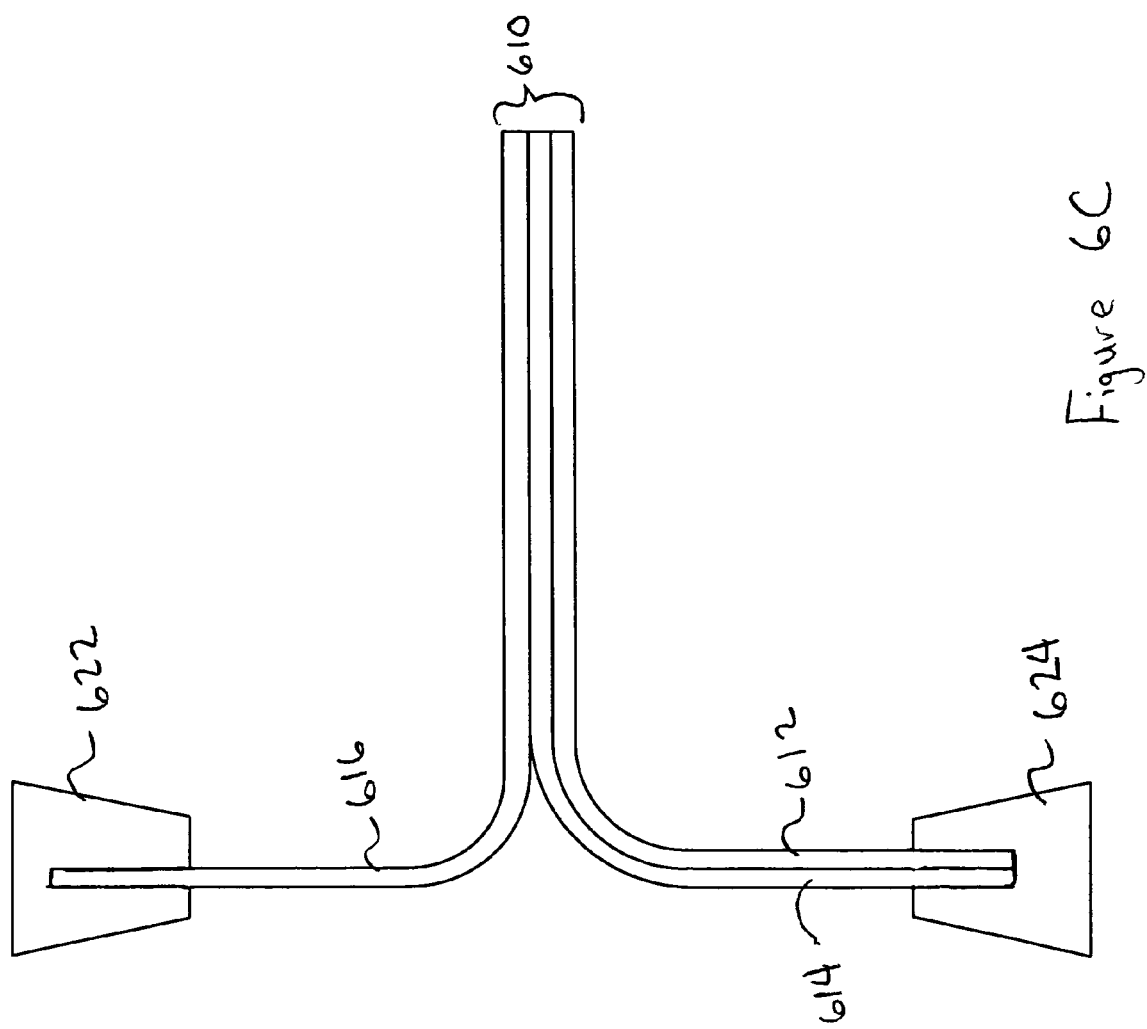
FIG. 6C shows the sample of FIGS. 6A and 6B mounted on the clamps of a tensile tester.
Figure 6D:
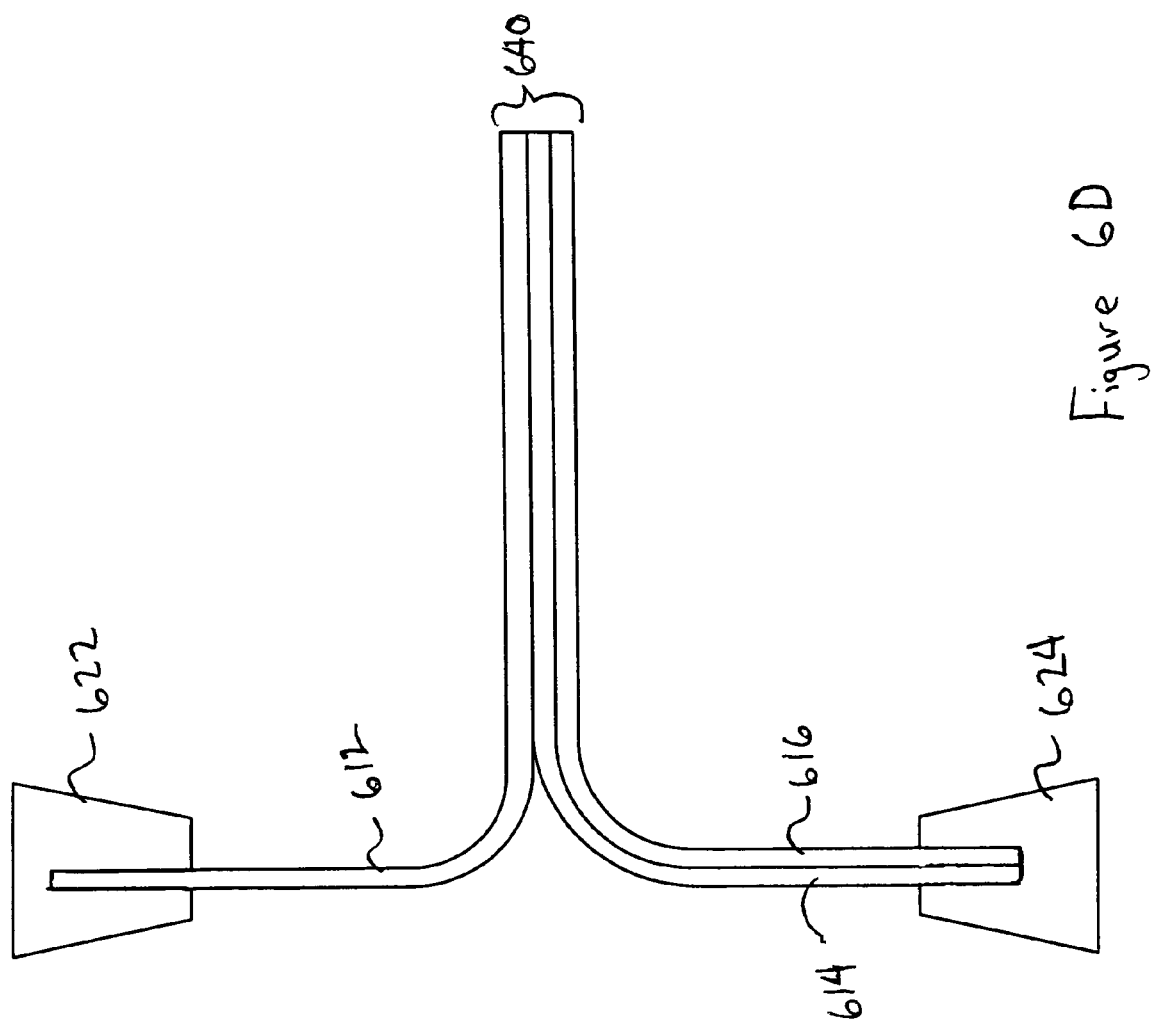
FIG. 6D shows a sample, prepared in a similar manner to that of FIGS. 6A and 6B, mounted on the clamps of a tensile tester.

Sample Preparation and Test:
1. As shown in FIG. 6A, a sample 610 stretch laminate should have a length 646 which is 18 cm long and cut substantially parallel to a plurality of adhesive stripes 602 in the activation region. The sample 610 should have a width 647 of 2.5 cm wide. Note that the sample 610 only includes the activation region. Tack down regions are not included in this test. The sample should be cut from a web of stretch laminate.
   As shown in FIG. 6B, the sample 610 includes a first substrate 616, an elastic film 614, and a second substrate 612. The first substrate 616 is adhesively attached to the elastic film 614, and the second substrate 612 is adhesively attached to the elastic film 614. The sample 610 is mechanically activated. The sample 610 is allowed to equilibrate for a period of 24 hours after mechanical activation.
2. Manually separate the first substrate 616 from the elastic film 614 from an end of the sample 610 for a distance of 2.5 cm in the test direction, i.e. parallel to the adhesive stripes. Note that neither the first substrate 616 nor the elastic film 614 should be torn. If either are torn, repeat step 1 of the sample preparation.
3. Zero the load cell according to manufacturer's instructions such that the load cell is reading between 0±0.5 grams force.
4. As shown in FIG. 6C, mount the sample 610 into the movable grip 622 and stationary grip 624. The first substrate 616 is mounted into the movable grip 622 while the elastic film 614 and the second substrate 612 are mounted in the stationary grip 624. The sample 610 is mounted into the grips in a manner such that there is a minimum amount of slack in the sample 610.
5. Start tensile tester and data collection devices simultaneously as provided by the manufacturer's instructions. Store the data from the tensile test.
6. Disregard results for the first 3 cm of the tensile test.
7. After first substrate 616 has been completely removed from elastic film 614 and second substrate 612, stop the tensile tester.
8. Remove the sample 610 from the tensile tester.
9. A shown in FIG. 6D, prepare a second sample 640 which includes the same components as described in step 1 and FIGS. 6A and 6B of the sample preparation section above.
10. Manually separate the second substrate 612 from the elastic film 614 for which the peel strength is to be measured for a distance of 2.5 cm in the test direction, i.e. parallel to the adhesive stripes. Note that neither the second substrate 612 nor the elastic film 614 should be torn. If either are torn, repeat the sample preparation of step 9.
11. Zero the load cell according to manufacturer's instructions such that the load cell is reading between 0±0.5 grams force.
12. As shown in FIG. 6D, mount the second sample 640 into a movable grip 622 and a stationary grip 624. The first substrate 616 and the elastic film 614 are mounted into the stationary grip 624 while the second substrate 612 is mounted in the movable grip 622. The second sample 640 is mounted into the grips in a manner such that there is a minimum amount of slack in the second sample 640.
13. Start tensile tester and data collection devices simultaneously as provided by the manufacturer's instructions. Store the data from the tensile test.
14. After second substrate 612 has been completely removed from elastic film 614 and first substrate 616, stop the tensile tester.
15. Remove the second sample 640 from the tensile tester.

End of testing method for determining the bond strength of a stretch laminate.

The method for determining the creep resistance of a stretch laminate is discussed below. All of the steps associated with this test method should be performed in an environment of 23±1° C. and 50%±2% relative humidity except where otherwise noted.

Sample Preparation:
1. Enough representative absorbent articles should be selected from the retail packaging of the absorbent article to conduct all required tests. Each article should be disassembled in a manner that minimally disturbs the structure of any layers comprising the absorbent article. For example, adhesively joined layers can be separated by first freezing them using a freeze spray such as Freeze-It® as is available from ITW Chemtronics Americas of Kennesaw, Ga. Other samples may need to be cut from the absorbent article.

2. Remove an ear panel or side panel which is to be tested, from the acquired absorbent articles. The ear panel or side panel was described further in regard to FIG. 5. Note that the ear panel or side panel is removed such that the tack down regions and the activation regions are in tact for testing. If the sample is damaged, then another sample is removed from the same absorbent article.

Figure 7:
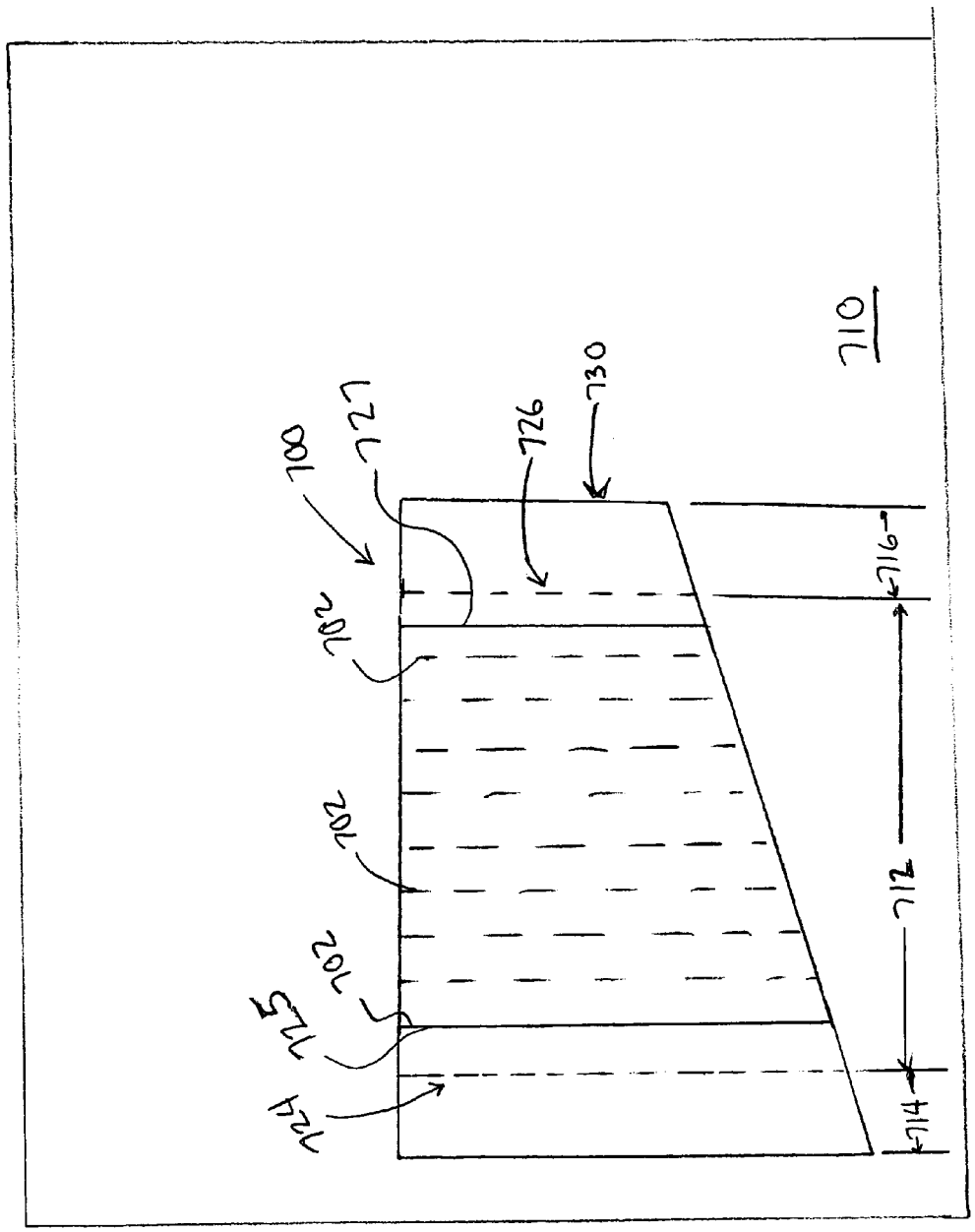
FIG. 7 shows a sample for a creep resistance test mounted on a cardboard backing.

3. As shown in FIG. 7, a sample 700 is mounted to a cardboard backing 710. A first tack down region 714 should be attached to the cardboard backing 710 via masking tape or a plurality of staples. Any attachment means can be used; however, the first tack down region 714 must be attached to the cardboard backing 710 such that the first tack down region 714 does not move relative to the cardboard backing 710. The cardboard backing 710 is sized such that the sample 700 can extend up to 100% of its original length and still be completely on the cardboard backing 710.

4. Mark a first line 725 parallel to a plurality of adhesive stripes 702 on an adhesive stripe in an activation region 712 which is immediately adjacent to an inner edge 724 of the of the first tack down region 714. Also, with the sample 700 in a relaxed state, mark a second line 727 parallel to the plurality of adhesive stripes 702 on an adhesive stripe in the activation region 712 which is immediately adjacent to an inner edge 726 of a second tack down region 716.

5. Pulling on the second tack down region 716, extend the sample 700 such that the sample 700 is extended 200%, i.e. two times the length of the sample 700 in its relaxed state. Mark a third line parallel to the plurality of adhesive stripes 702 on the cardboard backing 710 which corresponds to the end edge 730 of the sample 700 when the sample 700 is extended to 200%.

6. Attach the second tack down region 716 to the cardboard backing 710 such that the end edge 730 is on the third line from step 5. Again, any attachment means can be used; however, the second tack down region 716 should be attached to the cardboard backing 710 such that the second tack down region 716 does not move relative to the cardboard backing 710.

7. Place cardboard backing 710 with sample 700 attached thereto in a chamber which can deliver a constant temperature of 37.5° C.

8. The cardboard backing 710 with the sample 700 will remain in the chamber for 12 hours.

9. Remove the cardboard backing 710 with the sample 700 thereon from the chamber.

10. Inspect the sample 700. Check the first tack down region 714, the activation region 712, and the second tack down region 716 to determine whether the elastic film of the sample 700 has receded from either or both of the first tack down region 714 and the second tack down region 716. If a portion of the elastic film has visibly receded from the first tack down region 714 to the first line 725, then the sample 700 fails. Similarly, if a portion of the elastic film has visibly receded from the second tack down region 716 to the second line 727, then the sample 700 fails.

This concludes the test for creep resistance.

The method for determining the strain and strain rate which the stretch laminate experiences is discussed below.

Figure 8A:
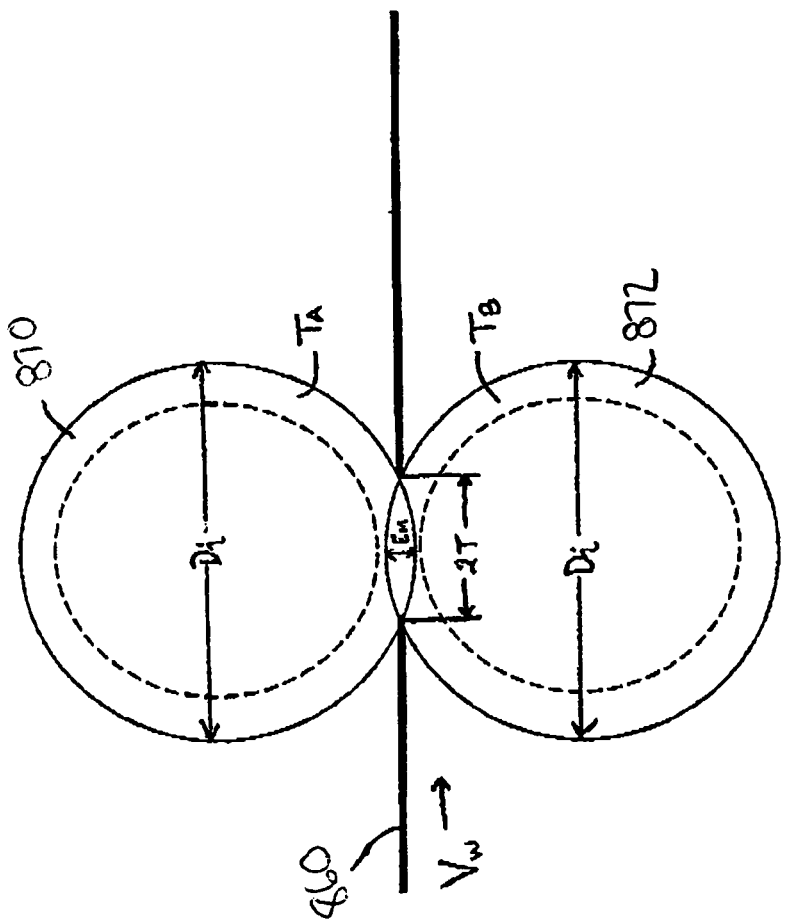
FIG. 8A shows a schematic of a mechanical activation apparatus.

Regarding FIG. 8A, several parameters from the mechanical activation process should be measured or determined. One of the parameters that should be determined is the web velocity $V_w$, i.e., the velocity at which an intermediate laminated structure 860 runs between a first activation roll 870 and a second activation roll 872 in the mechanical activation process. Another parameter which should be determined is a depth of engagement E(t) of the first and second teeth $T_A$ and $T_B$ on the first and second activation rolls 870 and 872 as a function of time; the pitch p of the first and second teeth $T_A$ and $T_B$ on the first and second activation rolls 870 and 872; and the diameter Di of the first and second activation rolls 870, 872 should be determined as well.

The depth of engagement of first and second teeth $T_A$ and $T_B$ engaging a given point on the laminated structure as a function of time is defined by the following equations:

$$T = a\cos\left[1 - \frac{E_M}{Di}\right] \cdot \left[\frac{Di}{2 \times Vw}\right]$$

$$E(t) = E_M - Di \cdot \left[1 - \cos\left[a\cos\left(1 - \frac{E_M}{Di}\right) \cdot \left(\frac{t}{T} - 1\right)\right]\right]$$

$E_M$ is equal to the maximum depth of engagement of the first and second teeth $T_A$ and $T_B$ which can be measured from the first and second activation rolls 870 and 872;

Di is equal to the diameter of the first and second activation rolls 870 and 872 (it is presumed that the activation rolls 870 and 872 have the same diameter);

t is equal to the process time and has a value from 0 to 2T; and

T is equal to one-half of the total time a given point on the laminated structure is engaged by teeth $T_A$ and $T_B$ on the first and second activation rolls.

Figure 8B:
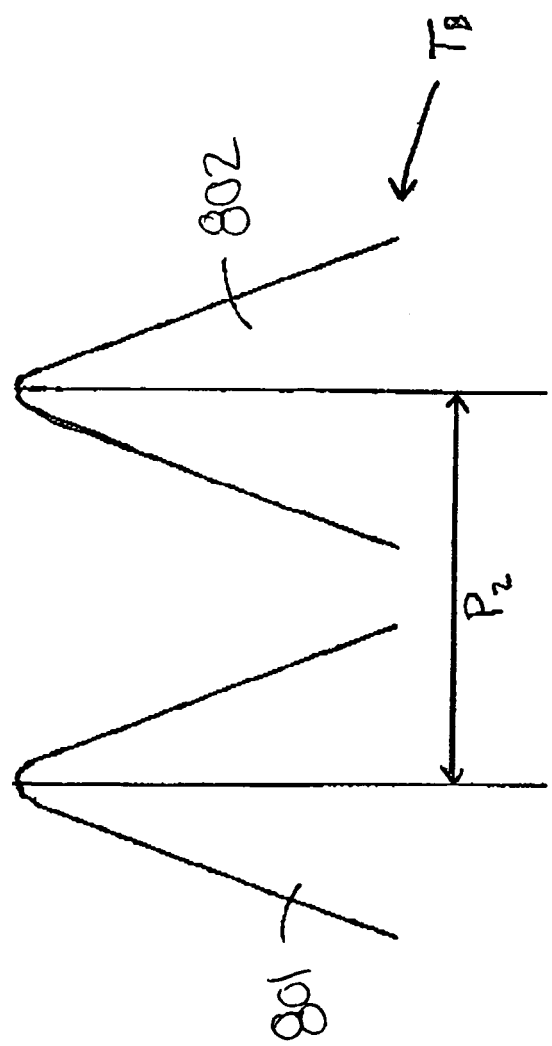
FIG. 8B shows a close up view of a plurality of teeth from an activation roll of the mechanical activation apparatus of FIG. 8A.

As shown in FIG. 8B, the pitch of teeth $T_B$ can be equal to the distance $p_2$ between the vertical centerlines of a first tooth 801 and a second tooth 802 on an activation roll. The pitch of the teeth $T_A$ should be measured similarly.

The radius of either the first or second activation rolls spans from a first tooth tip radius of a first tooth to the axis of rotation of the activation roll. The diameter Di of the activation roll is twice the radius. The tooth tip radius is described further with regard to FIGS. 9 and 10.

Note that all of the equations herein are based on an assumption that the diameter $D_i$ of the first activation roll is equal to the diameter $D_i$ of the second activation roll. Where the diameters of the first and second activation rolls differ, the method for determining strain and strain rate in a mechanical activation process herein remains the same with the exception that the equations corresponding to the variables mentioned above must be re-derived taking into account the difference in roll diameters. One skilled in the art would be able to modify the equations provided herein in the event that the diameters of the first activation roll and the second activation roll differed.

Figure 9:
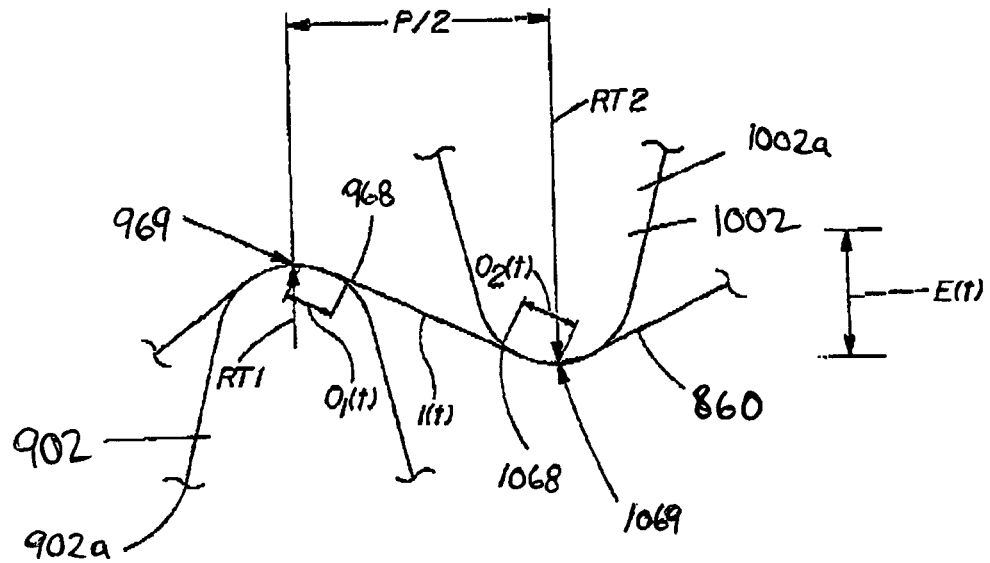
FIG. 9 is a schematic illustration of a first tooth and a second tooth engaging a laminated structure.
Figure 10:
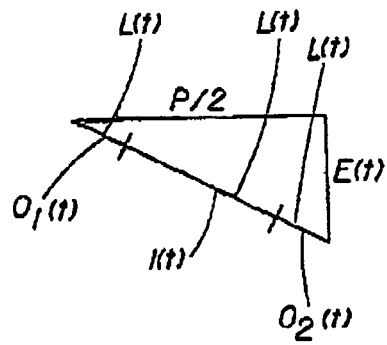
FIG. 10 is a schematic illustration of various dimensions illustrated in FIG. 9.

Regarding FIGS. 9 and 10, strain (t) and strain rate (t) experienced by the intermediate laminated structure 860 during the mechanical activation process can be determined using the equations provided below. A first tooth 902 and a second tooth 1002 on the first and second activation rolls, respectively, are shown engaged with the intermediate laminated structure 860. A portion of the intermediate laminated structure 860 extends between a center point 969 on the first tooth 902 to a center point 1069 on the second tooth 1002. The depth to which the first tooth 902 and the second tooth 1002 are engaged is defined by E(t) as discussed previously. The initial gage length lf of the the intermediate laminated structure 860, prior to being stretched by the first tooth 902 and the second tooth 1002, is equal to one-half of the pitch p of the teeth 902 and 1002, i.e., p/2. The processed or stretched length of the intermediate laminated structure 860 as a function of time, i.e., L(t), is determined using the following equation:

$$L(t) = O_1(t) + O_2(t) + I(t) \qquad 5$$

where $O_1(t)$ is equal to a section of the intermediate laminated structure 860 engaged by the first tooth 902 and extending from the tooth center point 969 to a final tooth tangent point 968;

where $O_2(t)$ is equal to a section of the intermediate laminated structure 860 engaged by the second tooth 1002 and extending from the tooth center point 1069 to a final tooth tangent point 1068; and I(t) is equal to an intermediate section of the intermediate laminated structure 860 not engaged by either the first tooth 902 or the second tooth 1002 and extending between the final tooth tangent points 968 and 1068. For all of the following equations, the variables as listed below are described as follows:

p is equal to the pitch of the teeth 902 and 1002;

r is equal to the radius RT1 of an outer tip portion 902*a* of the first tooth 902 and is also equal to the radius RT2 of an outer tip portion 1002*a* of the second tooth 1002.

E(t) is equal to the depth to which the first tooth 902 and the second tooth 1002 engage one another as a function of time, and is determined by the equation which is discussed above.

I(t) is defined by the following equation:

$$I(t) = \sqrt{(p/2)^2 + (E(t) - 2r)^2 - (2r)^2}$$

O(t) is defined by the following equations:

$$O(t) = O_1(t) + O_2(t).$$

When $E(t) - 2r \geq 0$, O(t) is defined by the following equation:

$$O(t) = \left[ \begin{array}{c} \pi - a\cos\sqrt{\dfrac{(2r)^2}{(E(t) - 2r)^2 + (p/2)^2}} - \\ a\sin\sqrt{\dfrac{(p/2)^2}{(E(t) - 2r)^2 + (p/2)^2}} \end{array} \right] \cdot 2r$$

When $E(t) - 2r \leq 0$, O(t) is defined by the following equation:

$$O(t) = \left[ \begin{array}{c} -a\cos\sqrt{\dfrac{(2r)^2}{(E(t) - 2r)^2 + (p/2)^2}} + \\ a\sin\sqrt{\dfrac{(p/2)^2}{(E(t) - 2r)^2 + (p/2)^2}} \end{array} \right] \cdot 2r$$

When $E(t) - 2r \geq 0$, S(t) is defined by the following equations:

$$\text{Strain}(t) = \left( \dfrac{2 \cdot O(t) + I(t)}{p/2} - 1 \right)$$

$$\text{Strain}(t) = \left( \dfrac{\left( \begin{array}{c} \pi - a\cos\sqrt{\dfrac{(2r)^2}{(E(t) - 2r)^2 + (p/2)^2}} - \\ a\sin\sqrt{\dfrac{(p/2)^2}{(E(t) - 2r)^2 + (p/2)^2}} \end{array} \right) \cdot 2r + \sqrt{(p/2)^2 + (E(t) - 2r)^2 - (2r)^2}}{p/2} - 1 \right)$$

When $E(t) - 2r \leq 0$, S(t) is defined by the following equations:

$$\text{Strain}(t) = \left( \dfrac{2 \cdot O(t) + I(t)}{p/2} - 1 \right)$$

$$\text{Strain}(t) = \left( \dfrac{\left( \begin{array}{c} -a\cos\sqrt{\dfrac{(2r)^2}{(E(t) - 2r)^2 + (p/2)^2}} + \\ a\sin\sqrt{\dfrac{(p/2)^2}{(E(t) - 2r)^2 + (p/2)^2}} \end{array} \right) \cdot 2r + \sqrt{(p/2)^2 + (E(t) - 2r)^2 - (2r)^2}}{p/2} - 1 \right)$$

The average strain rate (t) can be determined by taking the first derivative of Strain(t). The first derivative of Strain(t) can be derived using, for example, a commercially available math processing software package such as Mathcad version 11.0 manufactured by Mathsoft Inc. located in Cambridge, Mass.

Final strain ($S_f$) is defined by the following equation:

$$S_f = [(L_f - L_0)/L_0]$$

where $L_f$ is the final length, after processing, of the intermediate laminated structure 860; and $L_0$ is the initial length, prior to processing, of the intermediate laminated structure 860 that is equal to p/2.

$S_f$ is determined using the equation for Strain(t) with t=T.

This concludes the test method for determining the strain and strain rate experienced by a laminated structure during mechanical activation.

A test method for determining the number of defects in a stretch laminate is discussed below.

A defect on a laminated structure caused by the mechanical activation process may include a hole. In fact, the majority of defects which occur on stretch laminates because of the mechanical activation process are holes. For example, during the mechanical activation process, holes can be created in a substrate or elastic film. For purposes of the present invention, a hole is defined as an opening in the substrate, elastic film, or both, which is greater than or equal to about 1 mm in diameter when the laminated structure is stretched under a force of 9.8N. The hole is then measured to the nearest millimeter while under a tension of 9.8N.

The number of defects is measured from a 5 m sample of the stretch laminate after mechanical activation. For example, a stretch laminate, not constructed in accordance with the present invention, can exhibit in excess of 8.5 defects/5 m of stretch laminate. A reduction in the number of defects in stretch laminates of the present invention can range anywhere from about a 0% reduction to about a 100% reduction in the number of defects. Thus, the term reduction includes those embodiments which utilize less adhesive while maintaining peel force and creep resistance criteria without increasing the number of defects.

The difference between a stretch laminate of the present invention and a conventional stretch laminate is shown below in Table I. Several stretch laminates were constructed from a first nonwoven having a basis weight of 27 gsm and a second nonwoven having a basis weight of 27 gsm. The first and second nonwovens are sold under the trade name Prosoft™ and manufactured by RKW AG Rheinische Kunststoffwerke, located in Worms, Germany. A film having a basis weight of 67 gsm was sandwiched between the first and second nonwovens. The film was manufactured by Tredegar and has a model number of X29969. An adhesive was applied to both the first and the second nonwovens at 14 gsm. In all of the stretch laminates created, the tack down regions received adhesive which was 5 mm wide and applied at both ends of each stretch laminate, and the activation regions received a plurality of adhesive stripes which had a width of about 1 mm. The adhesive was manufactured by Bostik located in Wauwatosa, Wis., and has a model number of H2861. The stretch laminates were mechanically activated by rolls having a pitch of 3.81 mm and diameters of 20.24 inch (51.41 cm) at varying speeds and varying depths of engagement.

Note that some stretch laminates were constructed in accordance with conventional stretch laminates while other stretch laminates were constructed in accordance with the present invention. The stretch laminates constructed in accordance with conventional stretch laminates are located in Table I under the column heading "1 mm spacing between stripes". The stretch laminates constructed in accordance with the present invention are located in Table I under the column heading "2 mm spacing between stripes". The stretch laminates listed under the heading "3 mm spacing between stripes" are provided to show the effect of too little adhesive on the properties of the stretch laminates. See Table I below.

Table I provides data for the number of defects in the stretch laminates per 5 m of the stretch laminate. Table I also provides data for the peel force of the stretch laminates at various depths of engagement. For stretch laminates constructed in accordance with the present invention, the peel force values are greater than those of the conventional stretch laminates or are within 20% of the peel force values of the conventional stretch laminates.

Finally, Table I also provides data regarding the creep resistance test for the stretch laminates at various depths of engagement. As previously stated, the creep resistance test does not allow for numerical data. As shown, stretch laminates constructed in accordance with the present invention passed the creep resistance test at all of the depths of engagement for which it was tested.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for wearing about the lower torso of a wearer, the disposable absorbent article having a first waist region, a second waist region, and a crotch

TABLE I

| Depth of Engagement (mm) | Strain Rate ($s^{-1}$) | 1 mm spacing between stripes | 2 mm spacing between stripes | 3 mm spacing between stripes |
|---|---|---|---|---|
| | | Number of Defects per 5 m of stretch laminate | | |
| 5 mm | 511 | 0 | 0 | 0 |
| 6 mm | 598 | 0.3 | 0 | 0 |
| 7 mm | 678 | 8.6 | 0.3 | 0 |
| 8 mm | 756 | 19 | 1.6 | 0.3 |
| | | Peel Force (grams force/cm) | | |
| 5 mm | 511 | | | |
| First nonwoven from stretch laminate | | 137.6 | 228.4 | 271.2 |
| Second nonwoven from stretch laminate | | 158 | 128.48 | 79.5 |
| 6 mm | 598 | | | |
| First nonwoven from stretch laminate | | 149.8 | 165.1 | 194.6 |
| Second nonwoven from stretch laminate | | 116.2 | 224.3 | 38.7 |
| 7 mm | 678 | | | |
| First nonwoven from stretch laminate | | 128 | 119.3 | 141.7 |
| Second nonwoven from stretch laminate | | 131.5 | 109.1 | 63.2 |
| 8 mm | | No data | No data | No data |
| | | Creep Resistance | | |
| 5 mm | 511 | Passed | Passed | Passed |
| 6 mm | 598 | Passed | Passed | Passed |
| 7 mm | 678 | Passed | Passed | Passed |
| 8 mm | 756 | No data | No data | No data | region disposed between the first waist region and the second waist region, the disposable absorbent article further comprising:
- a chassis comprising:
  - a topsheet;
  - a backsheet attached to at least a portion of the topsheet; and
  - an absorbent core disposed between at least a portion of the topsheet and the backsheet; and
- at least one elastically extensible ear panel having an inner edge and an outer edge, wherein the inner edge is attached to the first waist region or the second waist region, and wherein the at least one elastically extensible ear panel further comprises:
  - an elastic film;
  - a first substrate attached to the elastic film via an adhesive disposed between the first substrate and the elastic film;
  - a second substrate attached to the elastic film via an adhesive disposed between the second substrate and the elastic film;
  - a first tack down region disposed along the inner edge;
  - a second tack down region disposed along the outer edge; and
  - an activation region disposed between the first tack down region and the second tack down region;
- wherein the adhesive in a portion of the activation region includes a plurality of stripes having a distance between adjacent stripes and each stripe having a stripe width, wherein a ratio of the stripe width to the distance between adjacent stripes is about 0.75;
- and wherein the adhesive in another portion of the activation region includes a plurality of stripes having a distance between adjacent stripes and each stripe having a stripe width, wherein a ratio of the stripe width to the distance between adjacent stripes is about 0.5.

2. A disposable absorbent article for wearing about the lower torso of a wearer, the disposable absorbent article having a first waist region, a second waist region, and a crotch region disposed between the first waist region and the second waist region, the disposable absorbent article further comprising:
- a chassis comprising:
  - a topsheet;
  - a backsheet attached to at least a portion of the topsheet; and
  - an absorbent core disposed between at least a portion of the topsheet and the backsheet; and
- at least one elastically extensible ear panel having an inner edge and an outer edge, the inner edge being attached to the first waist region or the second waist region, the elastically extensible ear panel further comprising:
  - an elastic film;
  - a first substrate attached to the elastic film via an adhesive disposed between the first substrate and the elastic film;
  - a second substrate attached to the elastic film via an adhesive disposed between the second substrate and the elastic film;
  - a first tack down region disposed along the inner edge;
  - a second tack down region disposed along the outer edge; and
  - an intermediate region disposed between the first tack down region and the second tack down region;
- wherein the adhesive in a portion of the intermediate region includes a plurality of stripes having a width of less than 1 mm, the distance between adjacent stripes being 1.5 mm; and wherein the adhesive in another portion of the intermediate region includes a plurality of stripes having a width of less than 1 mm, the distance between adjacent stripes being 2 mm; and wherein the Peel Force value of the first substrate and the elastic film is between about 119 g/cm and about 271 g/cm and the Peel Force value of the second substrate and the elastic film is between about 63 g/cm and about 128 g/cm.

* * * * *